United States Patent [19]
Arenberg et al.

[11] Patent Number: 6,045,528
[45] Date of Patent: Apr. 4, 2000

[54] INNER EAR FLUID TRANSFER AND DIAGNOSTIC SYSTEM

[75] Inventors: Irving K. Arenberg; Michael H. Arenberg, both of Englewood, Colo.

[73] Assignee: IntraEar, Inc., Greenwood Village, Colo.

[21] Appl. No.: 08/874,208

[22] Filed: Jun. 13, 1997

[51] Int. Cl.[7] .................................................. A61M 1/00
[52] U.S. Cl. ................................ 604/28; 604/49; 604/54
[58] Field of Search .................................. 604/27, 43, 48, 604/93, 269, 174, 271, 280, 28, 49, 54; 128/DIG. 26

[56] References Cited

U.S. PATENT DOCUMENTS

| | | |
|---|---|---|
| 2,642,065 | 6/1953 | Negri . |
| 3,528,419 | 9/1970 | Joechle et al. . |
| 4,034,759 | 7/1977 | Haerr . |
| 4,159,719 | 7/1979 | Haerr . |
| 4,175,563 | 11/1979 | Arenberg et al. . |
| 4,244,377 | 1/1981 | Grams . |
| 4,250,878 | 2/1981 | Jacobsen et al. . |
| 4,297,748 | 11/1981 | Moloy . |
| 4,320,758 | 3/1982 | Eckenhoff et al. . |
| 4,419,092 | 12/1983 | Jacobsen et al. . |
| 4,650,474 | 3/1987 | De Backer .............................. 604/43 |
| 4,757,807 | 7/1988 | Densert et al. . |
| 4,874,368 | 10/1989 | Miller et al. . |
| 4,968,297 | 11/1990 | Jacobsen et al. . |
| 4,971,076 | 11/1990 | Densert et al. . |
| 4,976,966 | 12/1990 | Theeuwes et al. . |
| 5,037,380 | 8/1991 | Jacobsen et al. . |
| 5,171,216 | 12/1992 | Dasse et al. ............................. 604/43 |
| 5,176,654 | 1/1993 | Schreiber ............................... 604/181 |
| 5,219,334 | 6/1993 | Tsukada . |
| 5,236,413 | 8/1993 | Feiring . |
| 5,281,287 | 1/1994 | Lloyd et al. . |
| 5,282,785 | 2/1994 | Shapland et al. . |
| 5,286,254 | 2/1994 | Shapland et al. . |
| 5,304,134 | 4/1994 | Kraus et al. . |
| 5,364,343 | 11/1994 | Apolet et al. ............................. 604/43 |
| 5,417,657 | 5/1995 | Hauer ...................................... 604/43 |
| 5,419,312 | 5/1995 | Arenberg et al. . |
| 5,419,777 | 5/1995 | Hofling .................................. 604/264 |
| 5,421,818 | 6/1995 | Arenberg . |
| 5,451,233 | 9/1995 | Yock ..................................... 604/264 |
| 5,474,529 | 12/1995 | Arenberg . |
| 5,476,446 | 12/1995 | Arenberg . |
| 5,776,111 | 7/1998 | Tesio ..................................... 604/264 |

FOREIGN PATENT DOCUMENTS

| | | |
|---|---|---|
| 223763 | 5/1987 | European Pat. Off. . |
| WO89/11882 | 12/1989 | WIPO . |
| WO92/11895 | 7/1992 | WIPO . |

OTHER PUBLICATIONS

Kingma, G., et al., "Chronic drug infusion into the scala tympani of the guinea pig cochlea," *Journal of Neuroscience Methods*, 45:127–134 (1992).

(List continued on next page.)

*Primary Examiner*—Wynn Wood Coggins
*Assistant Examiner*—Jennifer R. Sadula
*Attorney, Agent, or Firm*—Jay K. Malkin; Klaas, Law, O'Meara & Malkin, P.C.

[57] ABSTRACT

An apparatus for transferring fluids into and out of the inner ear through the round window membrane. The apparatus includes a cover member sized for placement over the round window niche. Fluid delivery and fluid extraction conduits are provided which are operatively connected to the cover member so that fluids can pass therethrough. The cover member is positioned over the niche to create a fluid-recieving zone between the cover member and the round window membrane. As a result, fluids can be delivered into or withdrawn from the zone. Alternatively, a single conduit may be used for fluid delivery and extraction. Another variation uses a compressible cover member positioned within the round window niche to form a fluid-receiving zone between the cover member and the round window membrane. The same type of conduit system described above is attached to the compressible cover member.

10 Claims, 6 Drawing Sheets

OTHER PUBLICATIONS

House, W.F., "Subarachnoid shunt for drainage of hydrops: a report of 146 cases", *Laryngoscope* 75:1547–1551 (1965).

Brookler, K.H. et al., "Closed Loop Water Irrigator System", *Otolaryngol Head Neck Surg.*, 87:364–365 (May–Jun. 1979).

Kiil, F., "Molecular mechanism of osmosis", *American Journal of Physiology*, 256–260: (Apr. 1989).

Portmann, M., "Electrophysiological correlates of endolymphatic hypertension and endolymphatic hydrops: an overview of electrcochleography (ECOG)", *Inner Ear Surgery*, 241–247 (1991).

Satoh, Y. et al., "The effects of inline filtration on delivery of gentamicin at various flow rates", *Keio J. Med.*, vol. 41:(1), pp. 16–20 (Mar. 1992).

Erickson, D., "The hole story, fine–pore membranes remove viruses from biological drugs", *Scientific American*, vol. 267(3), pp. 163–164 (Sep. 1992).

Pillsbury, H.C., III et al. (ed.), *Operative Challenges in Otolaryngology–Head and Neck Surgery*, Yearbook Medical Publishers, Inc., Chicago, 93–101: (1990)–(article therein presented in Chapt. 7 entitled "Nondestructive Surgery for Vertigo" Approach of I. Kaufman Arenberg, et al.).

Pillsbury, H.C., III et al. (ed.), *Operative Challenges in Otolarynology–Head and Neck Surgery*, Yearbook Medical Publishers, Inc., Chicago, 139–145: (1990)—(article therein presented in Chapt. 10 entitled "Cochlear Implants"Approach of William M. Luxford et al.).

INNER EAR FLUID TRANSFER AND DIAGNOSTIC SYSTEM

BACKGROUND OF THE INVENTION

The present invention generally relates to an apparatus for therapeutically treating and/or analyzing conditions of the inner ear, and more particularly to a multi-functional medical apparatus for use in connection with the middle and inner ear in which the apparatus is capable of (1) delivering therapeutic agents including various medicines in fluid form to internal ear (e.g. inner ear) structures; (2) extracting, withdrawing, or exchanging fluid materials from the inner ear; (3) transferring fluid materials into and out of the inner ear via the round window membrane so that items (1) and (2) can be accomplished; (4) enabling middle and inner ear structures to be electrophysiologically monitored using electrocochleography ("ECoG") procedures; and (5) altering the permeability of the round window membrane in the ear for a variety of therapeutic purposes.

In order to treat ear disorders, it may often be necessary to deliver therapeutic agents to various ear tissues in a controlled, safe, and efficient manner. For example, a variety of structures have been developed which are capable of delivering/administering therapeutic agents into the external auditory canal of the outer ear. U.S. Pat. No. 4,034,759 to Haerr discloses a hollow, cylindrical tube manufactured of sponge material (e.g. dehydrated cellulose) which is inserted into the external auditory canal of a patient. When liquid medicines are placed in contact with the tube, it correspondingly expands against the walls of the auditory canal. As a result, accidental removal of the tube is prevented. Furthermore, medicine materials absorbed by the tube are maintained in contact with the walls of the external auditory canal for treatment purposes. Other absorbent devices designed for treatment of the external auditory canal and related tissue structures are disclosed in U.S. Pat. No. 3,528,419 to Joechle, U.S. Pat. No. 4,159,719 to Haerr, and U.S. Pat. No. 2,642,065 to Negri. The Negri patent specifically discloses a medicine delivery device with an internally-mounted, frangible medicine container which, when broken, releases liquid medicines into an absorbent member.

However, the delivery of therapeutic agents in a controlled and effective manner is considerably more difficult with respect to tissue structures of the inner ear (e.g. those portions of the ear surrounded by the otic capsule bone and contained within the temporal bone which is the most dense bone tissue in the entire human body). The same situation exists with respect to tissue materials which lead into the inner ear (e.g. the round window membrane). Exemplary inner ear tissue structures of primary importance for treatment purposes include but are not limited to the cochlea, the endolymphatic sac/duct, the vestibular labyrinth, and all of the compartments (and connecting tubes) which include these components. Access to the above-described inner ear tissue regions is typically achieved through a variety of structures, including but not limited to the round window membrane, the oval window/stapes footplate, the annular ligament, the otic capsule/temporal bone, and the endolymphatic sac/endolymphatic duct, all of which shall be considered middle-inner ear interface tissue structures as described in greater detail below. In addition, as indicated herein, the middle ear shall be defined as the physiological air-containing tissue zone behind the tympanic membrane (e.g. the ear drum) and ahead of the inner ear.

The inner ear tissues described above are of minimal size and only readily accessible through microsurgical procedures. In order to treat various diseases and conditions associated with inner ear tissues, the delivery of medicines to such structures is often of primary importance. Representative medicines which are typically used to treat inner ear tissues include but are not limited to urea, mannitol, sorbitol, glycerol, lidocaine, xylocaine, epinephrine, immunoglobulins, sodium chloride, steroids, heparin, hyaluronidase, aminoglycoside antibiotics (streptomycin/gentamycin), antioxidants, neurotrophins, nerve growth factors, various therapeutic peptides, and polysaccharides. Of particular interest in this list are compounds which are used to alter the permeability of the round window membrane within the ear. Likewise, treatment of inner ear tissues and/or fluid cavities may involve altering the pressure, volume, electrical activity, and temperature characteristics thereof. Specifically, a precise balance must be maintained with respect to the pressure of various fluids within the inner ear and its associated compartments. Imbalances in the pressure and volume levels of such fluids can cause various problems, including but not limited to conditions known as endolymphatic hydrops, endolymphatic hypertension, perilymphatic hypertension, perilymphatic hydrops, perilymphatic fistula, intracochlear fistula, Meniere's disease, and ruptures in various membrane structures within the ear.

Of further interest regarding the delivery of therapeutic agents to the middle ear, inner ear, and middle-inner ear interface tissues are a series of related and co-owned patents, namely, U.S. Pat. Nos. 5,421,818; 5,474,529, and 5,476,446 all to Arenberg. Each of these patents discloses a medical treatment apparatus designed to deliver fluid materials to internal ear structures. U.S. Pat. No. 5,421,818 describes a treatment system which includes a tubular stem attached to a reservoir portion with an internal cavity designed to retain a supply of therapeutic fluid compositions therein. The side wall of the reservoir portion further comprises fluid transfer means (e.g. pores or a semi-permeable membrane). Contact between the fluid transfer means and the round window membrane in a patient allows fluid materials to be delivered on-demand to the round window membrane, followed by diffusion of the fluid materials through the membrane into the inner ear. U.S. Pat. No. 5,474,529 involves a therapeutic treatment apparatus with a plurality of reservoir portions (e.g. a first and a second reservoir portion in a preferred embodiment) which are connected to multiple tubular stems that are designed for implantation into the endolymphatic sac and duct using standard surgical techniques. Finally, U.S. Pat. No. 5,476,446 discloses a therapeutic treatment apparatus which includes a reservoir portion for retaining liquid medicine materials therein, a first tubular stem on one side of the reservoir portion, and a second tubular stem on the opposite side of the reservoir portion. The second stem is designed to reside within the external auditory canal of a patient lateral to the ear drum, while the first stem is sized for placement within an opening formed in the stapes footplate/annular ligament so that medicine materials in fluid form can be delivered into the inner ear from the reservoir portion (which resides in the middle ear cavity medial to the ear drum).

Notwithstanding the systems described above, the present invention involves an improved medical treatment apparatus which provides many additional benefits. In accordance with the claimed invention, a unique and specially-designed treatment system is disclosed which is capable of performing a wide variety of basic functions including but not limited to (1) the repeatable and sustained active/passive delivery of therapeutic agents directly into the inner ear through the round window membrane; (2) the simultaneous measurement of inner ear electrical potentials (evoked or otherwise) using a technique known as "electrocochleography" (hereinafter "ECoG") which is discussed in greater detail below; (3) the controlled withdrawal, exchange, or replacement of inner ear fluid materials via the round window membrane; (4) the delivery of therapeutic fluid compositions to the round window membrane in a manner which is rapid, efficient, controllable, and uses a minimal number of steps and procedures; (5) the transfer of therapeutic fluid compositions to the round window membrane in a highly site-specific manner; (6) the removal of fluid materials from the round window membrane in a localized manner with minimal losses into adjacent tissue regions; (7) the ability to deliver and withdraw/exchange fluid materials from the inner ear at a precisely controlled rate which is readily undertaken using minimally-invasive surgical procedures; and (8) accomplishment of all the above-described goals using a system which is readily applicable to multiple patients having different sized ear structures Accordingly, the present invention represents an advance in the art of inner ear treatment, diagnosis, and medicine delivery as described in detail below

SUMMARY OF THE INVENTION

It is an object of the present invention to provide an inner ear fluid transfer and diagnostic system which enables the efficient delivery of fluid materials (e.g. therapeutic agents) to selected inner ear tissues and tissue regions.

It is another object of the invention to provide an inner ear fluid transfer and diagnostic system which allows the efficient removal or exchange of fluid materials from selected inner ear tissues and tissue regions.

It is another object of the invention to provide an inner ear fluid transfer and diagnostic system in which fluid materials are transferred/exchanged into and out of the inner ear directly through middle-inner ear interface tissues (e.g. the round window membrane).

It is another object of the invention to provide an inner ear fluid transfer and diagnostic system which enables the sustained transfer of fluid materials into and out of the inner ear (via the round window membrane) in a controlled, repeatable, and uniform manner.

It is another object of the invention to provide an inner ear fluid transfer and diagnostic system which facilitates the formation of a sealable inner ear fluid-receiving, transfer, and exchange zone at the point of entry into the inner ear (e.g. within the round window niche as further described below).

It is another object of the invention to provide an inner ear fluid transfer and diagnostic system which enables variable amounts of selected fluid materials to be transferred into and out of the inner ear including microgram/nanogram quantities of such materials (which is especially important when pharmacological agents are being delivered).

It is another object of the invention to provide an inner ear fluid transfer and diagnostic system which allows the delivery of fluid materials to the round window membrane and the removal of fluid materials therefrom in a highly site-specific manner while avoiding substantial leakage into surrounding tissue regions.

It is a further object of the invention to provide an inner ear fluid transfer and diagnostic system of small size which is readily inserted into a patient using minimally-invasive microsurgical procedures.

It is a further object of the invention to provide an inner ear fluid transfer and diagnostic system which, in one particular embodiment, enables the controlled delivery, exchange, and removal of fluid materials from the inner ear via the round window membrane in a manner wherein the fluid materials being delivered are maintained separately from the fluid materials being removed through the use of separate fluid delivery and fluid extraction conduits. As a result, efficient fluid transfer is accomplished while avoiding or minimizing cross-contamination between the fluids being removed and the fluids being delivered. This procedure is especially useful in situations involving drugs or other therapeutic agents which must be delivered in very precise amounts (e.g. microgram/nanogram quantities) or when such materials need to be supplied in a given sequence and at controlled time intervals.

It is an even further object of the invention to provide an inner ear fluid transfer and diagnostic system having a subsystem (e.g. an electrode assembly) which is capable of delivering and receiving electrical signals (e.g. electrical potentials/current) to and from the inner ear via the round window membrane.

The present invention involves a highly effective and minimally-invasive apparatus and method for the controlled and site-specific transfer (e.g. "microdosing") of physician-specified fluid materials into and out of the inner ear via the round window membrane (which is centrally located within the round window niche). The invention described herein offers numerous benefits and represents a significant advance in the art of middle and inner ear diagnosis/treatment. The following summary of the claimed apparatus and method represents a general overview of the invention which discusses the features of primary importance. A more detailed, specific, and enabling disclosure of the invention shall be presented later in the Detailed Description of Preferred Embodiments.

A first embodiment of the claimed invention involves a medical treatment apparatus and method for transferring fluid materials into and out of the inner ear of a human subject via the round window membrane as previously noted. The apparatus specifically includes a cover member sized for placement over the main opening leading into the round window niche of the subject (discussed further below) so that a sealed fluid-receiving zone is created within the round window niche between (1) the cover member [the upper or external boundary of the fluid-receiving zone]; and (2) the round window membrane [the lower or internal boundary of the fluid-receiving zone]. In physiological terms, the fluid-receiving zone described above constitutes the "inner ear fluid transfer space" between the cover member and the round widow membrane within the round window niche. In a preferred and optimum embodiment, the cover member is manufactured from a biologically-inert, medical-grade material selected from the group consisting of silicone rubber, latex rubber, and plastic. The term "plastic" as used herein shall encompass a wide variety of materials including but not limited to polycarbonate, polyester, polyethylene, polypropylene, polyvinyl chloride, nylon, cellophane, and other comparable materials. Next, a tubular fluid delivery conduit is provided which is operatively connected to the cover member. The fluid delivery conduit includes an open first end, an open second end, and an internal passageway extending continuously through the fluid delivery conduit from the afirst end to the second end. The first end of the fluid delivery conduit is optimally passed through the cover member as discussed in greater detail below. In a preferred embodiment, this is accomplished by passing the fluid delivery conduit through at least one opening in the cover member, followed by secure attachment of the fluid delivery conduit within the opening using many possible connection systems including but not limited to adhesives, frictional engagement, and the like. As a result, the fluid delivery conduit can deliver selected therapeutic fluid compositions through the cover member to the round window membrane during use of the claimed apparatus. When the fluid delivery conduit is mounted in position relative to the cover member as indicated above, the second end will be remotely spaced from the cover member (e.g. within the external auditory canal of the patient being treated) so that therapeutic fluid compositions can be readily administered when needed. However, the term "operatively connected" as used in connection with the cover member and fluid delivery conduit shall encompass any attachment configuration which enables fluid materials to pass through both the fluid delivery conduit and the cover member. For example, this term would include placement of the first end of the fluid delivery conduit flush with the opening through the cover member so that no part of the first end extends outwardly from the cover member.

With continued reference to the claimed treatment apparatus, a tubular fluid extraction conduit (which is a separate structure from the fluid delivery conduit) is provided which is operatively connected to the cover member. The fluid extraction conduit includes an open first end, an open second end, and an internal passageway extending continuously through the fluid extraction conduit from the first end of the fluid extraction conduit to the second end thereof. In a preferred embodiment, both the fluid extraction conduit and the fluid delivery conduit are of substantially equal length and made of the same construction materials (discussed below).

In the same manner described above in connection with the fluid delivery conduit, the fluid extraction conduit is passed through the cover member. This is accomplished in a preferred embodiment by passing the fluid extraction conduit through at least one opening in the cover member, followed by secure attachment of the fluid extraction conduit within the opening using many possible connection systems including but not limited to adhesives, frictional engagement, and the like. It should also be noted that the fluid delivery conduit and the fluid extraction conduit may be passed through and secured within the same opening through the cover member, or a separate, individual opening may be provided in the cover member for each conduit. In this regard, both of these attachment methods shall be deemed functionally equivalent. Likewise, the term "operatively connected" as used in connection with the cover member and fluid extraction conduit shall encompass any attachment configuration which enables fluid materials to pass through both the fluid extraction conduit and the cover member. For example, this term would include placement of the first end of the fluid extraction conduit flush with the opening through the cover member so that no part of the first end extends outwardly from the cover member.

Attachment of the fluid extraction conduit to the cover member in the foregoing manner will enable residual fluid materials which are present at or adjacent the round window niche/round window membrane to be extracted (preferably using known suction-based or aspiration methods and the like) through the internal passageway of the fluid extraction conduit. Extraction may be "active" as discussed above or "passive" wherein fluid extraction results from osmotic forces or other physical factors. Likewise, when the fluid extraction conduit is secured in position as discussed above, the second end of the fluid extraction conduit will be remotely spaced from the cover member in order to readily facilitate the complete removal of residual fluid materials by the treating physician without additional invasive surgical procedures.

The apparatus described above may also include electrical potential transmission means secured to at least one or both of the fluid delivery conduit and the fluid extraction conduit by adhesive affixation techniques and other comparable methods. Likewise, the term "secured" as used in connection with the electrical potential transmission means can also encompass a situation in which this component is directly incorporated (e.g. molded) into the side wall of one or both of the fluid delivery and fluid extraction conduits. The electrical potential transmission means is used to transmit electrical potentials into and out of the inner ear through the round window membrane. In a preferred embodiment discussed in substantial detail below, the electrical potential transmission means will consist of an elongate conductive member (e.g. a metallic wire or strip with a ball or spoon-shaped tip) which is affixed to at least one or both of the fluid delivery conduit and the fluid extraction conduit. By placing at least a portion of the elongate conductive member (e.g. a portion which is exposed and not covered by any insulation materials) in direct physical contact with the round window membrane during use of the claimed apparatus, evoked or non-evoked electrical potentials (signals) may be transmitted to and from the membrane for therapeutic analysis and other purposes using various techniques encompassed within the term "electrocochleography" or "ECoG". Iontophoresis techniques may also be facilitated using the components listed above, with this term being defined to involve a process in which electrical energy is used to alter the permeability characteristics of the round window membrane.

In a modification of the apparatus discussed above, only a single conduit (hereinafter designated as a "fluid transfer conduit") is provided instead of the dual conduits (e.g. the separate fluid delivery conduit and the fluid extraction conduit). All of the other components, features, and structures described in connection with the dual conduit system are equally applicable to the single-conduit version of the claimed apparatus. Specifically, a cover member is again used which is sized for placement over the main opening leading into round window niche of the subject so that a sealed fluid-receiving zone (or "inner ear fluid transfer space") is created within the round window niche between (1) the cover member [the upper or external boundary of the fluid-receiving zone]; and (2) the round window membrane [the lower or internal boundary of the fluid-receiving zone]. The cover member is produced from the same materials listed above in connection with the dual conduit system. The single fluid transfer conduit (which is operatively connected to the cover member) includes an open first end, an open second end, and an internal passageway extending continuously through the conduit from the first end to the second end. The fluid transfer conduit is passed through the cover member in the same manner discussed above. In particular, the fluid transfer conduit is again routed through at least one opening in the cover member. The fluid transfer conduit is then secured in position within the opening using various attachment systems including adhesives, frictional engagement, and the like. When the fluid transfer conduit is attached to the cover member in this manner, the second end of the fluid transfer conduit will be remotely spaced from the cover member. This overall design enables the delivery of therapeutic fluid compositions to the round window membrane in a highly effective/controlled manner, and will likewise allow residual fluid materials that are present at or adjacent the round window membrane (e.g. within the fluid-receiving zone inside the round window niche) to be extracted using suction-based methods, aspiration processes, and the like. Likewise, the term "operatively connected" as used in connection with the cover member and fluid transfer conduit shall encompass any attachment configuration which enables fluid materials to pass through both the fluid transfer conduit and the cover member. For example, this term would include placement of the first end of the fluid transfer conduit flush with the opening through the cover member so that no part of the first end actually extends outwardly from the cover member.

As noted above in the dual conduit version of the claimed apparatus, the single conduit system may also include electrical potential transmission means secured to the fluid transfer conduit by adhesive affixation techniques and other comparable methods. The electrical potential transmission means is again used to transmit electrical potentials into and out of the inner ear through the round window membrane. The electrical potential transmission means will typically consist of an elongate conductive member (e.g. a metallic wire or strip having a ball or spoon-shaped tip) which is affixed to the fluid transfer conduit. By placing at least a portion of the elongate conductive member (e.g. the electrical potential transmission means) in direct physical contact with the round window membrane during use of the claimed apparatus, evoked and non-evoked electrical potentials (signals) may be transmitted to and from the membrane for therapeutic analysis and other purposes using ECoG methods. Likewise, iontophoresis techniques may also be implemented using the components listed above.

Both of the foregoing systems will effectively enable the transfer of fluid materials into and out of the inner ear via the round window membrane using the "inner ear fluid transfer space" discussed above. The dual conduit version of the claimed apparatus is particularly useful in situations where cross-contamination between (1) the fluid materials being delivered into the ear; and (2) the residual fluid materials being removed or exchanged is not desired. This is especially important in situations where therapeutic agents (e.g. drugs) need to be delivered in very precise (e.g. microgram, microliter, or nanoliter) amounts over controlled time periods.

A brief summary of the procedures involved in transferring fluid materials into and out of the inner ear using the above-described systems will now be provided. With reference to the dual conduit version of the claimed apparatus, it is initially inserted into the subject so that the cover member is positioned within the middle ear of the subject. Specific methods for accomplishing this step (including the required surgical procedures) will be discussed further below in the Detailed Description of Preferred Embodiments section. The cover member is then positioned over the main opening leading into the round window niche (e.g. over the top of niche) so that a fluid-receiving zone or "inner ear fluid transfer space" is created within the niche between the cover member and the round window membrane.

Next, a supply of therapeutic fluid compositions is delivered into and through the internal passageway of the fluid delivery conduit (e.g. by conventional hypodermic delivery systems, microsyringes, osmotic mini-pumps, servosyringes, electromechanical pumps, and the like) so that the therapeutic fluid compositions pass through the cover member, enter the fluid-receiving zone within the round window niche, and come in contact with the round window membrane. The therapeutic fluid compositions will then pass through the round window membrane (e.g. by diffusion, osmosis, and the like) and move into the inner ear for the treatment thereof. Any residual fluid materials which remain within the fluid-receiving zone between the cover member and the round window membrane after delivery of the therapeutic fluid compositions (e.g. residual, undiffused therapeutic agents, tissue fluids from the inner ear, and the like) may thereafter be withdrawn through the internal passageway of the fluid extraction conduit so that they can be removed from the subject. In a preferred embodiment, withdrawal of the residual fluid materials is accomplished by applying suction to the second end of the fluid extraction conduit (which is remotely spaced from the cover member and preferably positioned within the external auditory canal) in order to withdraw the residual fluid materials through the internal passageway of the fluid extraction conduit. As noted above, the use of separate fluid delivery and fluid extraction conduits avoids cross-contamination of the incoming and outgoing fluids which is particularly important in situations where controlled, precise, and contamination-free drug delivery is desired.

If a selected electrical potential transmission means (e.g. an elongate conductive member) is used in connection with the claimed treatment apparatus, electrical potentials may be transmitted into and out of the inner ear via the round window membrane by placing at least a portion of the elongate conductive member against and in direct physical contact with the round window membrane. This may be accomplished by appropriate physical manipulation of the treatment apparatus within the middle ear as specifically discussed in the Detailed Description of Preferred Embodiments section so that the elongate conductive member comes in contact with the round window membrane. Electrical potentials received from the inner ear via the round window membrane and the elongate conductive member are especially valuable from a diagnostic standpoint, and are analyzed using an ECoG system operatively connected to the elongate conductive member.

Comparable fluid transfer techniques are used in connection with the single-conduit version of the claimed apparatus in which a single fluid transfer conduit is employed instead of the separate fluid delivery and fluid extraction conduits. However, the steps to be used in transferring fluid materials into and out of the inner ear using this single-conduit system will be summarized for the sake of clarity and completeness. In accordance with the present invention, the apparatus is again inserted into the subject so that the cover member is located within the middle ear of the subject. The cover member is then positioned over main opening leading into the round window niche (e.g. over the top of niche) so that a fluid-receiving zone or "inner ear fluid transfer space" is created within the niche between the cover member and the round window membrane.

Next, a supply of therapeutic fluid compositions is delivered into and through the internal passageway of the fluid transfer conduit (e.g. by conventional hypodermic delivery systems, microsyringes, osmotic mini-pumps, servosyringes, electromechanical pumps, and the like) so that the therapeutic fluid compositions pass through the cover member, enter the fluid-receiving zone, and come in contact with the round window membrane. The therapeutic fluid compositions will thereafter pass through the round window membrane by diffusion, osmosis, or other similar processes and move into the inner ear for the treatment of inner ear tissues. Any residual fluid materials which remain within the fluid-receiving zone between the cover member and the round window membrane (e.g. residual, undiffused therapeutic agents, tissue fluids from the inner ear, and the like) may thereafter be withdrawn through the internal passageway of the fluid transfer conduit so that they can be removed from the subject. In a preferred embodiment, withdrawal of the residual fluid materials is accomplished by applying suction to the second end of the fluid transfer conduit in order to withdraw the residual fluid materials through the internal passageway of the conduit. This is readily accomplished by the treating physician since the second end of the fluid transfer conduit is remotely spaced from the cover member (e.g. within the external auditory canal of the subject in a preferred embodiment). Since only a single conduit is involved in this version of the claimed system, the extraction of residual fluid materials from the fluid-receiving zone will typically take place after the desired therapeutic fluid compositions have been administered to the round window membrane/round window niche by the fluid transfer conduit.

If electrical potential transmission means (e.g. an elongate conductive member) is used in connection with this version of treatment apparatus, evoked or non-evoked electrical potentials may be transmitted into and out of the inner ear via the round window membrane by again placing at least a portion of the elongate conductive member against and in direct physical contact with the round window membrane. This may be accomplished by appropriate physical manipulation of the apparatus within the middle ear as discussed below. Electrical potentials received from the inner ear via the round window membrane and the elongate conductive member are of substantial value from a diagnostic standpoint, and are subsequently analyzed using an ECoG system operatively connected to the elongate conductive member.

In addition to the primary embodiments of the present invention discussed above (which both use a cover member placed over the top [main opening] of the round window niche), the claimed invention likewise involves an alternative system which also allows the effective transfer of fluid materials into and out of the inner ear via the round window membrane. This alternative system uses substantially the same theories of operation and procedural steps, but employs certain components which are dissimilar to those listed above. In particular, a different type of cover member is used which is mounted within the round window niche of a patient at a position above the round window membrane so that a fluid-receiving zone (e.g. "inner ear fluid transfer space") is created between (1) the cover member; and (2) the round window membrane. The round window niche includes a continuous, internal side wall comprised of bone compositions covered by mucosa which interacts with the cover member in this embodiment of the invention to provide an effective fluid barrier. Specifically, the cover member consists of a portion of flexible and compressible material which, during placement within the round window niche, is compressed and thereafter allowed to expand once the portion of compressible material is positioned within the round window niche. As a result, the cover member can engage the side wall of the round window niche and provide a fluid-tight seal within the niche, thereby forming the fluid-receiving zone ("inner ear fluid transfer space") between the cover member and the round window niche. Representative materials used to construct the portion of compressible material associated with the cover member in this alternative embodiment include but are not limited to polyethylene foam, polyether foam, polyester foam, polyvinyl chloride foam, polyurethane foam, and sponge rubber (e.g. synthetic or natural), all of which are of the closed cell variety, with such materials being non-fluid-absorbent in accordance with the substantial lack of open cells therein. Specifically, the non-fluid-absorbent character of these materials results from the closed cell character thereof which prevents fluid materials from being absorbed compared with open cell (absorbent) foam products.

Next, a tubular fluid delivery conduit is provided which is operatively connected to the cover member (e.g. the portion of compressible material discussed above). The fluid delivery conduit includes an open first end, an open second end, and an internal passageway extending continuously through the fluid delivery conduit from the first end to the second end. The fluid delivery conduit is then routed through the portion of compressible material. In a preferred embodiment, the fluid delivery conduit is preferably passed through at least one opening in the portion of compressible material, followed by attachment of the fluid delivery conduit within the opening using many possible connection systems including adhesives, frictional engagement, and the like. As a result, the fluid delivery conduit can deliver therapeutic fluid compositions through the cover member to the round window membrane (e.g. the fluid-receiving zone or "inner ear fluid transfer space") during use of the claimed apparatus. When the fluid delivery conduit is mounted in position relative to the cover member as indicated above, the second end of the conduit will be remotely spaced from the cover member (e.g. positioned within the external auditory canal of the patient in a preferred embodiment). It should again be noted that the term "operatively connected" as used in connection with the cover member and fluid delivery conduit shall encompass any attachment configuration which enables fluid materials to pass through both the fluid delivery conduit and the cover member. For example, this term would include placement of the first end of the fluid delivery conduit flush with the opening through the cover member or inside the cover member so that no part of the first end actually extends outwardly from the cover member.

In addition, a tubular fluid extraction conduit (which is separate from the fluid delivery conduit) is provided which is operatively connected to the cover member (e.g. the portion of compressible material discussed above). The fluid extraction conduit includes an open first end, an open second end, and an internal passageway extending continuously through the fluid extraction conduit from the first end to the second end. In a preferred embodiment, both the fluid extraction conduit and the fluid delivery conduit are of substantially equal length.

In the same manner described above in connection with the fluid delivery conduit, the fluid extraction conduit is routed through the portion of compressible material used to construct the cover member. Specifically, the fluid extraction conduit is passed through at least one opening in the portion of compressible material, followed by attachment of the fluid extraction conduit to and within the opening using various connection systems including adhesives, frictional engagement, and the like. It should also be noted that both the fluid delivery conduit and the fluid extraction conduit may be passed through and secured within the same opening through the cover member (e.g. the portion of compressible material), or may be maintained within separate openings in the cover member for each conduit. Both of these attachment methods shall be deemed functionally equivalent for the purposes of this invention. Likewise, the term "operatively connected" as used in connection with the cover member and fluid extraction conduit shall encompass any attachment configuration which enables fluid materials to pass through both the fluid extraction conduit and the cover member. For example, this term would include placement of the first end of the fluid extraction conduit flush with the opening through the cover member or inside the cover member so that no part of the first end actually extends outward from the cover member.

Attachment of the fluid extraction conduit to the cover member in the foregoing manner will enable residual fluid materials which are present within the sealed fluid-receiving zone to be extracted via the internal passageway of the fluid extraction conduit using suction-based methods and the like. Likewise, when the fluid extraction conduit is secured in position as discussed above, the second end of the fluid extraction conduit will be remotely spaced from the cover member (e.g. within the external auditory canal of the patient) in order to facilitate access to the fluid extraction conduit so that the complete removal of residual fluid materials can be accomplished.

The above-described apparatus may also include electrical potential transmission means secured to at least one or both of the fluid delivery conduit and the fluid extraction conduit by adhesive affixation techniques and other comparable methods. Likewise, the term "secured" as used in connection with the electrical potential transmission means can also encompass a situation in which this component is directly incorporated (e.g. molded) into the side wall of one or both of the fluid delivery and fluid extraction conduits. The electrical potential transmission means (discussed above) is again used to transmit evoked or non-evoked electrical potentials into and out of the inner ear through the round window membrane. In a preferred embodiment described in greater detail below, the electrical potential transmission means will consist of an elongate conductive member (e.g. a metallic wire or strip with a ball or spoon-shaped tip) that is secured to at least one or both of the fluid delivery conduit and the fluid extraction conduit. By placing at least a portion of the elongate conductive member (e.g. a portion which is exposed or uncovered by any insulating materials) in direct physical contact with the round window membrane during use of the claimed apparatus, evoked and non-evoked electrical potentials (signals) may be transmitted to and from the membrane for therapeutic analysis and other purposes using ECoG techniques, iontophoresis, and the like.

In a modification of the above-described alterative embodiment of the claimed apparatus, only a single conduit (hereinafter designated as a "fluid transfer conduit") is provided instead of the separate fluid delivery conduit and the fluid extraction conduit. All of the other components, features, and structures listed above in connection with the dual conduit version are equally applicable to the single conduit version of the claimed system. Specifically, a portion of flexible and compressible material is again used as the cover member. This material is produced from the same compositions listed above. The single fluid transfer conduit (which is operatively connected to the cover member) includes an open first end, an open second end, and an internal passageway extending continuously through the conduit from the first end to the second end. The fluid transfer conduit is then routed through the portion of compressible material used to construct the cover member. In a preferred embodiment, the fluid transfer conduit is passed through at least one opening in the portion of compressible material associated with the cover member, followed by affixation of the fluid transfer conduit within the opening using various connection systems discussed below including adhesives, frictional engagement, and the like. In this configuration, the second end of the fluid transfer conduit will be remotely spaced from the cover member (e.g. preferably within the external auditory canal of the patient). However, the term "operatively connected" as used in connection with the cover member and fluid transfer conduit shall again encompass any attachment configuration which enables fluid materials to pass through both the fluid transfer conduit and the cover member. For example, this term would include placement of the first end of the fluid transfer conduit flush with the opening through the cover member or inside the cover member so that no part of the first end actually extends outwardly from the cover member. Attachment of the fluid transfer conduit to the cover member (e.g. the portion of compressible material) in the foregoing manner will enable therapeutic fluid compositions to be delivered to the round window membrane and will likewise allow residual fluid materials which are present at or adjacent the round window membrane to be extracted using suction-based methods and the like.

In addition, as previously noted, this version of the claimed apparatus may also include electrical potential transmission means secured to the fluid transfer conduit by adhesive affixation techniques and other comparable methods. The electrical potential transmission means is again used to transmit electrical potentials into and out of the inner ear through the round window membrane. The electrical potential transmission means will likewise consist of an elongate conductive member (e.g. a metallic wire or strip having a ball or spoon-shaped tip) which is secured to the fluid transfer conduit. By placing at least a portion of the elongate conductive member (e.g. a portion which is exposed or uncovered by any insulating materials) in direct physical contact with the round window membrane during use of the claimed apparatus, evoked or non-evoked electrical potentials (signals) may be transmitted to and from the membrane for therapeutic analysis and other purposes using ECoG techniques, iontophoresis methods, and the like.

Both of the alternative systems described above (which use a portion of compressible material as the cover member) enable the creation of a fluid-receiving zone or "inner ear fluid transfer space" within the round window niche of a patient which facilitates the transfer of fluid materials into and out of the inner ear via the round window membrane. The dual conduit version of the claimed apparatus is particularly useful in situations where cross-contamination between (1) the fluid materials being delivered into the ear; and (2) the residual fluid materials being removed is not desired. This is especially important when controlled, precise, and contamination-free drug delivery (e.g. in microgram, microliter, or nanoliter amounts) is desired.

Operation of the alternative systems described above is substantially similar to the method steps previously discussed in connection with the primary embodiments of the invention. Regarding the alternative system which uses a separate fluid delivery conduit and fluid extraction conduit, the claimed apparatus is inserted into the patient so that the compressible cover member is positioned within the patient's middle ear. Specific methods for accomplishing this step (including the minimally-invasive surgical procedures that are needed) will be discussed below in the Detailed Description of Preferred Embodiments section. Once it is positioned within the middle ear, the portion of flexible and compressible material used as the cover member is subsequently inserted into the round window niche of the subject being treated. The portion of compressible material is compressed during insertion into the round window niche and thereafter expands once it is positioned within the niche. As a result, the cover member frictionally engages the bony side wall of the round window niche in order to provide a fluid-tight seal therein.

The cover member (which is sized to avoid filling the entire niche) is then positioned (e.g. by physical manipulation) directly above the round window membrane in the round window niche in order to form a fluid-receiving zone ("inner ear fluid transfer space") located between the cover member and the round window membrane. Specifically, the cover member forms the upper boundary of the fluid-receiving zone while the round window membrane forms the lower boundary of the zone. A supply of therapeutic fluid compositions is then delivered into and through the internal passageway of the fluid delivery conduit (e.g. by conventional hypodermic delivery systems, microsyringes, osmotic mini-pumps, servosyringes, electromechanical pumps, and the like) so that the therapeutic fluid compositions pass through the cover member, enter the fluid-receiving zone, and come in contact with the round window membrane. The therapeutic fluid compositions will then pass through the round window membrane by osmosis, diffusion or other similar processes and move into the inner ear for the treatment thereof. Any residual fluid materials which remain within the fluid-receiving zone between the cover member and the round window membrane (e.g. residual, undiffused therapeutic agents or tissue fluids from the inner ear) may thereafter be withdrawn through the internal passageway of the fluid extraction conduit so that the residual fluid materials can be removed from the patient. In a preferred embodiment, extraction of the residual fluid materials is accomplished by applying suction to the second end of the fluid extraction conduit (which preferably resides within the external auditory canal of the patient) in order to withdraw the residual fluid materials through the internal passageway of the fluid extraction conduit.

If electrical potential transmission means (e.g. an elongate conductive member) is used in connection with this embodiment of the treatment apparatus, electrical potentials may be transmitted into and out of the inner ear via the round window membrane by again placing at least a portion of the elongate conductive member against and in direct physical contact with the round window membrane. This may be accomplished by the appropriate physical manipulation of the treatment apparatus within the middle ear as specifically discussed in the Detailed Description of Preferred Embodiments section so that the elongate conductive member comes in contact with the round window membrane. Evoked or non-evoked electrical potentials received from the inner ear via the round window membrane and elongate conductive member are again of substantial value from a diagnostic standpoint, with such electrical potentials being analyzed using an ECoG system operatively connected to the elongate conductive member.

A comparable approach is likewise employed in connection with the single-conduit version of the claimed apparatus. However, the steps to be used will again be summarized for the sake of clarity and completeness. To transfer fluid materials into and out of the inner ear via the round window membrane using the single-conduit system, it is again inserted into the patient so that the compressible cover member is positioned within the patient's middle ear. The portion of flexible and compressible material used as the cover member is subsequently inserted into the round window niche of the patient being treated. The portion of compressible material is compressed during insertion into the round window niche and thereafter expands once it is positioned within the niche. As a result, the cover member frictionally engages the bony side wall of the round window niche in order to provide a fluid-tight seal therein. Again, the cover member is sized so that it does not completely fill the round window niche.

The cover member is then positioned (e.g. by physical manipulation) directly above the round window membrane in the round window niche in order to create a fluid-receiving zone ("inner ear fluid transfer space") located between the cover member and the round window membrane. The cover member specifically forms the upper boundary of the fluid receiving-zone while the round window membrane forms the lower boundary of the zone.

Next, a supply of therapeutic fluid compositions is delivered into and through the internal passageway of the fluid transfer conduit (e.g. by conventional hypodermic delivery systems, microsyringes, osmotic mini-pumps, servosyringes, electromechanical pumps, and the like) so that the therapeutic fluid compositions pass through the cover member, enter the fluid-receiving zone, and come in contact with the round window membrane. The therapeutic fluid compositions will then pass through the round window membrane and move into the inner ear by diffusion, osmosis, and the like for the treatment thereof. Any residual fluid materials which remain within the fluid-receiving zone between the cover member and the round window membrane (e.g. residual, undiffused therapeutic agents or tissue fluids from the inner ear) may thereafter be withdrawn through the internal passageway of the fluid transfer conduit so that the residual fluid materials are removed from the patient. To achieve optimal results, withdrawal of the residual fluid materials is again accomplished by applying suction to the second end of the fluid transfer conduit in order to extract the residual fluid materials through the internal passageway of the fluid transfer conduit. Since only a single conduit is involved in this embodiment, the extraction of residual fluid materials from the fluid-receiving zone will typically take place after the desired therapeutic fluid compositions have been delivered to the round window membrane as discussed above.

If electrical potential transmission means (e.g. an elongate conductive member) is used in connection with this version of treatment apparatus, electrical potentials may again be transmitted into and out of the inner ear via the round window membrane by placing at least a portion of the elongate conductive member against and in direct physical contact with the round window membrane. This may be accomplished by the appropriate physical manipulation of the apparatus within the middle ear as outlined below. Electrical potentials received from the inner ear via the round window membrane are of particular value from a diagnostic standpoint, with these potentials again being analyzed using an ECoG system operatively connected to the elongate conductive member.

The present invention represents an advance in the art of inner ear therapy, treatment, and diagnosis. The claimed treatment systems and methods provide numerous benefits and capabilities including: (1) the creation of a sealed fluid-receiving zone (e.g. "inner ear fluid transfer space") within the round window niche of a patient which enables the controlled and effective delivery of therapeutic fluid compositions to the inner ear via the round window membrane; (2) the delivery of therapeutic fluid compositions to the inner ear using minimally-invasive approaches which are readily accomplished with minimum patient discomfort; (3) the transfer of a wide variety of different therapeutic agents into the middle and inner ear in a sustained, controlled, and highly site-specific manner; (4) the removal of fluid materials from the inner ear, the round window niche, the round window membrane, and adjacent tissue regions in an efficient and thorough manner using a minimal amount of equipment and operating components; (5) the ability to electrocochleographically monitor evoked and non-evoked signals/potentials coming from the inner ear while simultaneously delivering therapeutic agents so that the effect of such agents can be immediately determined; (6) transmission into the middle and inner ear of various signals so that a diagnostic, electrophysiological analysis of internal ear structures can be made in a rapid manner; and (7) the development of a unique, multi-functional inner ear treatment and diagnostic system which enables all of the foregoing benefits to be achieved using a minimal amount of components, procedures, equipment, and technical personnel. For these reasons and the other reasons listed below, the claimed invention represents a substantial advance in the art of otological treatment and diagnosis.

These and other objects, features, and advantages of the invention will become readily apparent from the following Brief Description of the Drawings and Detailed Description of Preferred Embodiments.

DETAILED DESCRIPTION OF PREFERRED EMBODIMENTS

Figure 1:
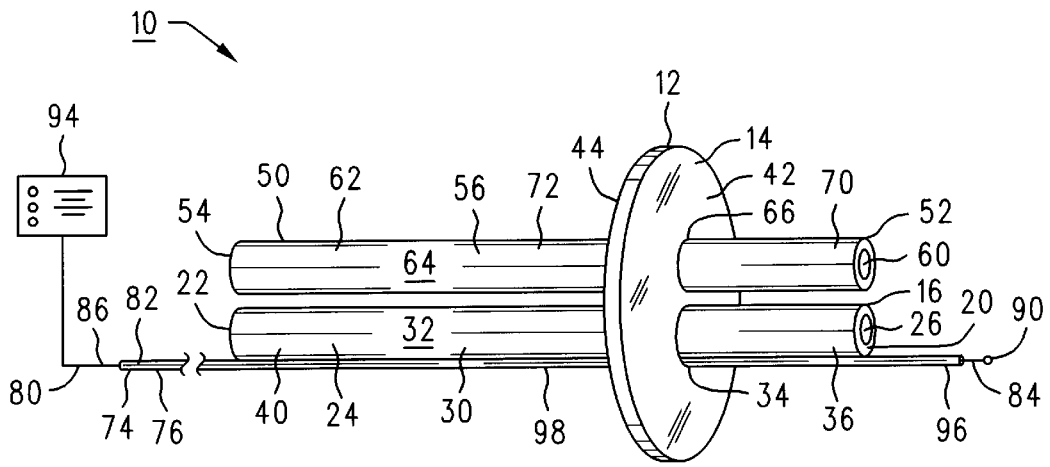
FIG. 1 is a front perspective view of a primary embodiment of the claimed fluid transfer and diagnostic apparatus.

As noted above, the present invention involves a unique and highly effective method for transferring fluid materials into and out of the inner ear via the intact round window membrane. The "round window membrane" consists of a thin, cellular membrane structure positioned within a cavity in the middle ear known as the "round window niche". Both of these structures are illustrated and discussed in U.S. Pat. No. 5,421,818 which is incorporated herein by reference. The round window membrane has a number of important physical features including a semi-permeable character which enables fluid materials to be readily transferred across the membrane by diffusion, osmosis, active transport, and the like as discussed further below. The round window membrane provides a number of unique opportunities regarding the transfer of fluid materials into and out of the inner ear through the membrane. For the purposes of this invention, both the round window membrane and the round window niche shall collectively be designated herein as "middle-inner ear interface tissue structures". Likewise, the middle ear shall be defined as the physiological air-containing tissue zone behind the tympanic membrane (e.g. the ear drum) and ahead of the inner ear. The "inner ear" basically consists of those portions of the ear contained within the temporal bone which is the most dense bone tissue in the entire human body. Exemplary inner ear tissue structures of primary importance include but are not limited to the cochlea, the endolymphatic sac/duct, the vestibular labyrinth, and all of the compartments/connecting tubes which include these components.

In order to treat various diseases and conditions associated with the inner ear, the delivery of medicines thereto is of primary importance. Representative medicines (also designated herein as "therapeutic fluid compositions") which are typically used to treat inner ear tissues include but are not limited to urea, mannitol, sorbitol, glycerol, xylocaine, epinephrine, antioxidants, immunoglobulins, sodium chloride, steroids, heparin, hyaluronidase, and aminoglycoside antibiotics (streptomycin/gentamycin). Likewise, the treatment of inner ear tissues and/or fluids may involve altering the pressure, volumetric, and temperature characteristics thereof. Specifically, a precise balance must be maintained in connection with the pressure of various fluids inside the inner ear and its associated compartments. Imbalances in inner ear fluid pressure levels can cause numerous problems, including but not limited to conditions known as endolymphatic hydrops, endolymphatic hypertension, perilymphatic hypertension, Meniere's disease, and perilymphatic hydrops as discussed in greater detail below.

It is a goal of the present invention to provide an effective method for transferring fluid materials into and out of the inner ear with a minimal degree of complexity and surgical intervention. The term "fluid materials" shall not be limited to any particular compositions and will include drugs, biologics, as well as liquid materials produced within the ear itself. Thus, the term "fluid materials" shall not be restricted in any manner and shall be defined to encompass to both liquid and gaseous compositions.

It is likewise a goal of the invention to provide an apparatus and method which create a sealed "fluid-receiving zone" (also known as an "inner ear fluid transfer space") within the middle ear ahead of the round window membrane in which various fluids can be delivered and/or withdrawn from the inner ear via the round window membrane. As discussed in substantial detail below, this will be accomplished by covering or otherwise blocking the main opening leading into the round window niche in order to create the fluid-receiving zone (e.g. "inner ear fluid transfer space") between (1) the selected cover member [which shall define the upper boundary of the fluid-receiving zone]; and (2) the round window membrane [which shall define the lower boundary of the fluid-receiving zone]. Fluid materials are delivered into and/or withdrawn from the fluid-receiving zone by one or more tubular conduits which pass through the cover member. This unique process and the creation of a sealed fluid-receiving zone within the round window niche provides a number of important benefits including the ability to precisely control and monitor the transfer of fluids into and out of the inner ear. In this regard, the present invention represents a significant advance in the art of inner ear treatment and diagnosis.

A. Fluid Treatment and Diagnostic Devices of the Present Invention

Figure 2:
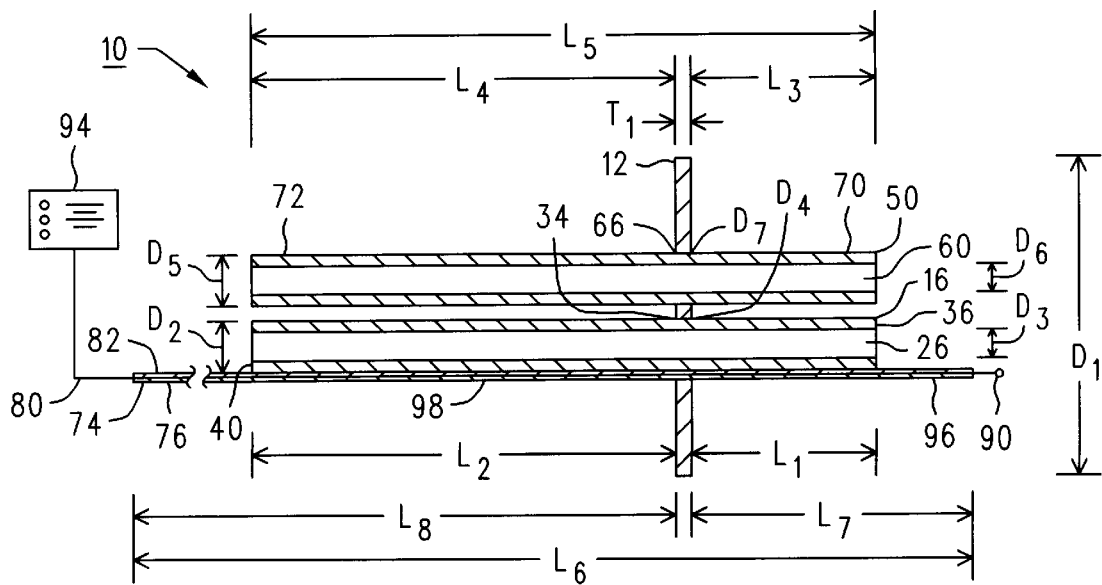
FIG. 2 is a cross-sectional view of the fluid transfer and diagnostic apparatus of FIG. 1.

Many different devices produced in accordance with the invention may be employed to achieve the goals listed above. Various embodiments of the claimed inner ear fluid transfer and diagnostic system will first be discussed in detail. Thereafter, the manner in which these systems are used in a patient will be described. With reference to FIGS. 1 and 2, a first treatment apparatus 10 is schematically illustrated in enlarged format for the sake of clarity. As shown in FIGS. 1 and 2, the apparatus includes a cover member 12 consisting of a flat, substantially plate-like body portion 14. However, the cover member 12 shall not be restricted to any particular shape or outward configuration. In this regard, the cover member 12 may either be flat or concave/convex depending on a variety of factors as determined by preliminary experimental testing involving the construction materials being employed and other factors. Regardless of the particular shape or configuration that is selected for the cover member 12, a representative embodiment will involve the use of a circular and flat cover member 12 as shown in FIGS. 1–2. In addition, the cover member 12 will be sufficiently sized to entirely cover (e.g. seal), the main opening which leads into the round window niche as discussed further below. The cover member 12 is specifically used to block the passage of fluid materials into and out of the round window niche during use of the apparatus 10 and, for this reason, should completely cover the top of the niche. In the representative, non-limiting embodiment of FIGS. 1–2, this may be accomplished by using a circular cover member 12 having a diameter "$D_1$" (FIG. 2) of about 6.5–8.0 mm. This diameter will be sufficient to cover the main opening in the round window niche which typically has a diameter of about 2.0–6.0 mm (depending on the particular patient under consideration).

The cover member 12 likewise has a preferred thickness "$T_1$" (FIG. 2) of about 0.1–0.7 mm and is constructed from a material which prevents the passage of fluids therethrough (e.g. the fluids that are typically encountered in the treatment and diagnosis of the inner ear.) Representative biologically-inert materials which may be selected for this purpose include but are not limited to silicone rubber, latex rubber, and plastic. The term "plastic" as used herein shall encompass a wide variety of materials including but not limited to polycarbonate, polyester, polyethylene, polypropylene, polyvinyl chloride, nylon, cellophane, and other comparable materials. However, the claimed invention shall not be restricted to any particular construction materials suitable for manufacturing the cover member 12, provided that such materials are capable of preventing the leakage or diffusion of fluids therethrough. Use of the representative materials listed above (along with the designated thickness values previously discussed) will enable the production of a cover member 12 with a sufficient level of durability and structural integrity to perform its intended function, namely, sealing of the round window niche to form an internal fluid-receiving zone or "inner ear fluid transfer space".

With continued reference to FIGS. 1–2, the apparatus 10 further includes at least one fluid delivery conduit 16 operatively connected (e.g. attached) thereto. The fluid delivery conduit 16 is used in this embodiment to introduce selected fluid (e.g. liquid) materials into the fluid-receiving zone (discussed below) through the cover member 12. The fluid delivery conduit 16 specifically includes an open first end 20, an open second end 22, and a medial portion 24 between the first and second ends 20, 22 (FIG. 1). In addition, the fluid delivery conduit is tubular in construction, with the term "tubular" being defined to encompass a structure which includes a continuous central passageway therethrough that is surrounded by an outer wall. As illustrated in FIG. 2, a central passageway 26 is provided which extends continuously through the conduit 16 from the first end 20 to the second end 22. Surrounding the central passageway 26 is a side wall 30 having an outer surface 32.

The fluid delivery conduit 16 is optimally circular in cross-section with a uniform external diameter "$D_2$" (FIG. 2) of about 0.5–2.0 mm. Likewise, in a preferred embodiment, the passageway 26 through the conduit 16 will have a uniform internal diameter "$D_3$" (FIG. 2) of about 0.1–0.6 mm which is sufficient to allow the adequate passage of therapeutic fluid compositions and other fluid materials therethrough. Representative biologically-inert construction materials which may be employed in connection with the fluid delivery conduit 16 include but are not limited to the same materials listed above in connection with the cover member 12, namely, silicone rubber, latex rubber, and plastic. The term "plastic" as used herein shall again encompass a wide variety of compositions including but not limited to polycarbonate, polyester, polyethylene, polypropylene, polyvinyl chloride, nylon, cellophane, and other comparable materials. It should be noted that the claimed invention shall not be restricted to any specific dimensions, construction materials, and other parameters in connection with the fluid delivery conduit 16. All of these items may be selected in accordance with a variety of factors including the intended use of the apparatus and the specific otological conditions being treated.

With continued reference to FIGS. 1–2, the fluid delivery conduit 16 is operatively connected to the cover member 12 as illustrated. The term "operatively connected" as used in connection with the cover member 12 and fluid delivery conduit 16 shall encompass any attachment configuration which enables fluid materials to pass through both the fluid delivery conduit 16 and the cover member 12. In the embodiment of FIGS. 1–2, the fluid delivery conduit 16 passes through the cover member 12 in a fluid-tight manner with the first end 20 of the conduit 16 being on one side of the cover member 12 and the second end 22 of the conduit 16 being on the other side. In the embodiment of FIGS. 1–2, this is specifically accomplished by providing a first opening 34 through the cover member 12 as illustrated. In a preferred embodiment, the first opening 34 will have a diameter "$D_4$" (FIG. 2) that is about 5–10% smaller than the external diameter "$D_2$" of the fluid delivery conduit 16 so that the conduit 16 may be tightly and securely engaged within the opening 34 (which is readily accomplished in accordance with the resilient character of the materials used to produce the cover member 12). In this regard, the diameter "$D_4$" of the first opening 34 will be about 0.45–1.9 mm in a representative, non-limiting embodiment.

Attachment of the fluid delivery conduit 16 to the cover member 12 is specifically accomplished by passing the first end 20 of the conduit 16 through the opening 34 in the cover member 12 until the medial portion 24 of the conduit 16 is securely engaged therein. The conduit 16 (e.g. the medial portion 24) may be maintained within the opening 34 by frictional engagement between these components or the use of a variety of conventional adhesive materials applied to both components including epoxy resin and/or cyanoacrylate adhesives known in the art. It is also contemplated that, during the production process associated with the apparatus 10, the cover member 12 may be integrally formed by thermal welding or molding processes known in the art directly on the outer surface 32 of the conduit 16. In this regard, the claimed apparatus 10 shall not be restricted to any particular construction methods. Furthermore, the term "operatively connected" as used in connection with the cover member 12 and the fluid delivery conduit 16 shall include placement of the first end 20 of the fluid delivery conduit 16 flush with the opening 34 through the cover member 12 so that no part of the first end 20 actually extends outwardly from the cover member 12.

As shown in FIGS. 1–2, the fluid delivery conduit 16 (after connection to the cover member 12) will be divided into a primary section 36 and a secondary section 40. In a representative and non-limiting embodiment, the primary section 36 (and the first end 20) of the conduit 16 will extend outwardly from the inner surface 42 of the cover member 12 (FIG. 1). As a result, during use of the apparatus 10, the primary section 36 and first end 20 will be entirely located within the round window niche of the patient being treated as discussed below. Likewise, to achieve proper use of the apparatus 10, the primary section 36 of the fluid delivery conduit 16 will have a length "$L_1$" (FIG. 2) of about 10–80 mm, although this value may be varied as needed and desired. The conduit 16 will also include a secondary section 40 as noted above which (along with the second end 22 of the conduit 16) extends outwardly from the outer surface 44 of the cover member 12. As a result, during use of the apparatus 10, the secondary section 40 and second end 22 of the conduit 16 will be located entirely outside of the round window niche and at least partially within the external auditory canal of the patient as defined above. To achieve proper use of the apparatus 10, the secondary section 40 will have a length "$L_2$" of about 20–150 mm although this value may be varied as needed and desired.

The basic purpose of the fluid delivery conduit 16 is to enable fluid materials (e.g. liquid drugs) to be passed through the cover member 12 for ultimate delivery into the fluid-receiving zone (e.g. "inner ear fluid transfer space") inside the round window niche for manipulation of the round window niche fluid environment. These materials can thereafter diffuse into the inner ear via the round window membrane as discussed above. However, in the embodiment of FIGS. 1–2, a separate conduit member is provided which may be used to withdraw various fluid materials from the fluid-receiving zone during or after the transfer of therapeutic fluid compositions into the zone by the fluid delivery conduit 16. The fluid materials which may be withdrawn from the fluid-receiving zone by this additional conduit include but are not limited to residual therapeutic agents and/or various inner ear fluids that have diffused through the round window membrane. For the sake of clarity and convenience, all of the materials to be withdrawn from the fluid-receiving zone in accordance with the present invention shall be designated herein as "residual" fluid materials regardless of their origin, with this term not being limited in any respect. To accomplish this goal in accordance with the embodiment of FIGS. 1–2, a separate fluid extraction conduit 50 is provided adjacent the fluid delivery conduit 16. In a preferred embodiment, both of the conduits 16, 50 will be identical in every respect including size/length parameters and construction materials. However, to provide a full and complete disclosure of the present embodiment, a detailed discussion of the fluid extraction conduit 50 will now be presented.

As noted above, the fluid extraction conduit 50 is specifically used in the embodiment of FIGS. 1–2 to remove selected fluid (e.g. liquid or gaseous) materials from the fluid-receiving zone through the cover member 12. The fluid extraction conduit 50 includes an open first end 52, an open second end 54, and a medial portion 56 between the first and second ends 52, 54 (FIG. 1). In addition, the fluid extraction conduit 50 is tubular in construction, with the term "tubular" being defined above. As illustrated specifically in FIG. 2, a central passageway 60 is provided within the conduit 50 which extends continuously through the conduit 50 from the first end 52 to the second end 54. Surrounding the central passageway 60 is a side wall 62 having an outer surface 64 (FIG. 1).

The fluid extraction conduit 50 is optimally circular in cross-section with a uniform external diameter "$D_5$" (FIG. 2) of about 0.5–2.0 mm. Likewise, in a preferred embodiment, the passageway 60 through the conduit 50 will have a uniform internal diameter "$D_6$" of about 0.1–0.6 mm which is sufficient to allow the adequate passage of fluid materials therethrough. Representative biologically-inert construction materials which may be employed in connection with the fluid extraction conduit 50 are the same as those listed above with respect to the fluid delivery conduit 16, namely, silicone rubber, latex rubber, and plastic. The term "plastic" as used herein shall again encompass a wide variety of compositions including but not limited to polycarbonate, polyester, polyethylene, polypropylene, polyvinyl chloride, nylon, cellophane, and other comparable materials.

With reference to FIGS. 1–2, the fluid extraction conduit 50 is operatively connected to the cover member 12 as illustrated. The term "operatively connected" as used in connection with the cover member 12 and fluid extraction conduit 50 shall encompass any attachment configuration which enables fluid materials to pass through both the fluid extraction conduit 50 and the cover member 12. In the embodiment of FIGS. 1–2, the fluid extraction conduit 50 passes through the cover member 12 in a fluid-tight manner with the first end 52 of the conduit 50 being on one side of the cover member 12 and the second end 54 of the conduit 50 being on the other side. In the embodiment of FIGS. 1–2, this is specifically accomplished by providing a second opening 66 through the cover member 12 as illustrated. In a representative embodiment, the second opening 66 will have a diameter "$D_7$" that is about 5–10% smaller than the external diameter "$D_5$" of the fluid extraction conduit 50 so that the conduit 50 may be tightly and securely engaged within the opening 66 (which is readily accomplished in accordance with the resilient character of the materials used to produce the cover member 12). In this regard, the diameter "$D_7$" of the second opening 66 will be approximately 0.45–1.9 mm in a representative, non-limiting embodiment.

Attachment of the fluid extraction conduit 50 to the cover member 12 is accomplished by passing the first end 52 of the conduit 50 through the second opening 66 in the cover member 12 until the medial portion 56 of the conduit 50 is securely engaged therein. The conduit 50 (e.g. the medial portion 56) may be maintained within the opening 66 by frictional engagement between these components or through the use of a variety of conventional adhesive materials including epoxy resin and/or cyanoacrylate adhesives known in the art. It is also contemplated that, during the production process associated with the apparatus 10, the cover member 12 may be integrally formed by thermal welding or molding processes known in the art directly on the outer surface 64 of the conduit 50 (and on the outer surface 32 of the fluid delivery conduit 16 as discussed above). Furthermore, instead of using the second opening 66, the fluid extraction conduit 50 may be passed through the first opening 34 along with the fluid delivery conduit 16, with the first opening 34 being suitably enlarged for this purpose. In such an embodiment, the first opening 34 would have an enlarged diameter "$D_4$" of about 0.9–3.8 mm to accommodate both of the conduits 16, 50 therein, although this range may be varied as needed and desired. Thus, while it is preferred that the present embodiment incorporate dual openings 34, 66 for each of the conduits 16, 50, the claimed apparatus 10 shall not be restricted to any particular construction methods or design configurations. It should also be noted that the term "operatively connected" as used in connection with the cover member 12 and the fluid extraction conduit 50 shall include placement of the first end 52 of the fluid extraction conduit 50 flush with the opening 66 through the cover member 12 so that no part of the first end 52 actually extends outward from the cover member 12.

However, in the embodiment of FIGS. 1–2, the fluid extraction conduit 50 (after connection to the cover member 12) is divided into a primary section 70 and a secondary section 72. In particular, the primary section 70 (and the first end 52) of the conduit 50 extends outwardly from the inner surface 42 of the cover member 12 (FIG. 1). During use of the apparatus 10, the primary section 70 and first end 52 will be entirely located within the round window niche of the patient being treated. Likewise, in a preferred embodiment, the primary section 70 of the fluid delivery conduit 50 will have a length "$L_3$" (FIG. 2) of about 10–80 mm which is substantially equal to the length "$L_1$" of the primary section 36 of the conduit 16, although this value may be varied as needed and desired. The conduit 50 will also include a secondary section 72 as noted above which (along with the second end 54 of the conduit 50) extends outwardly from the outer surface 44 of the cover member 12. Accordingly, during use of the apparatus 10, the secondary section 72 and second end 54 of the conduit 50 will be located entirely outside of the round window niche and at least partially within the external auditory canal of the patient being treated. To achieve proper use of the apparatus 10, the secondary section 70 will have a length "$L_4$" (FIG. 2) of about 20–150 mm which is substantially equal to the length "$L_2$" of the secondary section 40 of the conduit 16, although this value may be varied as needed and desired.

The completed treatment apparatus 10 is illustrated in FIGS. 1–2 and, in a preferred, non-limiting example, will have an overall length "$L_5$" (FIG. 2) of about 31–231 mm. Use of the apparatus 10 will be specifically discussed below in the section entitled "Methods of Use". However, at this time, it is important to note that the apparatus 10 and its use of dual (separate) fluid delivery and fluid extraction conduits 16, 50 is designed to avoid cross-contamination of the fluid materials being delivered and/or extracted from the fluid-receiving zone within the round window niche of the patient. This goal is important when precise amounts of therapeutic agents (e.g. microgram/nanogram/nanoliter quantities) are to be delivered in a highly controlled and precise manner. Having dual fluid delivery and extraction conduits 16, 50 enables the entire treatment process to be more carefully monitored, controlled, and assessed.

Finally, with continued reference to FIGS. 1–2, another feature of the apparatus 10 is illustrated. This feature, while optional in nature, provides numerous important benefits. The treatment apparatus 10 shown in FIGS. 1–2 includes electrical potential transmission means 74 fixedly secured to the fluid delivery conduit 16 for receiving evoked or non-evoked electrical potentials from middle/inner ear tissues and transmitting them out of the ear for detection and analysis. While the electrical potential transmission means 74 is shown in connection with the fluid delivery conduit 16, it is important to note that the electrical potential transmission means 74 may be operatively connected to at least one of the fluid delivery conduit 16 and the fluid extraction conduit 50. Specifically, the components associated with the electrical potential transmission means 74 (discussed below) may be attached to (A) the fluid delivery conduit 16; (B) the fluid extraction conduit 50; or (C) both of the conduits 16, 50. However, for the sake of clarity, the following discussion shall involve attachment of the electrical potential transmission means 74 to the fluid delivery conduit 16, with all of the information provided below being equally applicable to connection of the electrical potential transmission means 74 to the fluid extraction conduit 50.

In a preferred embodiment, the electrical potential transmission means 74 consists of an elongate conductive member 76 fixedly secured to the fluid delivery conduit 16 along the entire length thereof as illustrated. The elongate conductive member 76 specifically passes through the first opening 34 along with the medial portion 24 of the conduit 16. The size parameters listed above in connection with the first opening 34 should be sufficient to accommodate passage of both the fluid delivery conduit 16 and the elongate conductive member 76 therethrough. The elongate conductive member 76 may involve a variety of different structures. For example, it is preferred that the elongate conductive member 76 consist of a thin wire 80 (e.g. #27 gauge) manufactured from titanium. The wire 80 is preferably coated with a layer 82 of insulation thereon. Representative insulation materials include but are not limited to heat shrinkable Teflon® (polytetrafluoroethylene) tubing of a type well known in the art. The wire 80 further includes a proximal end 84 and a distal end 86 as illustrated (FIG. 1). The wire 80 (surrounded by the layer 82 of insulation) is fixedly secured to the fluid delivery conduit 16 of the apparatus 10 in any desired or suitable position thereon. In the embodiment of FIGS. 1–2, the wire 80 is attached to the conduit 16 of the apparatus 10 along the underside of the conduit 16. Attachment may be accomplished using a medical grade adhesive of the type set forth above (e.g. cyanoacrylate, epoxy resin, or other conventional adhesive materials). The term "secured" or "attached" as used in connection with the electrical potential transmission means 74/conductive member 76 can also encompass a situation in which this component is directly incorporated (e.g. molded) into the side walls 30, 62 of one or both of the fluid delivery and fluid extraction conduits 16, 50. It should also be noted that the conductive member 76 may involve other structures equivalent to the wire 80. For example, a substantially flat, flexible metallic strip (not shown) may be used in place of the wire 80, although the wire 80 is preferred.

As shown in FIGS. 1–2, the wire 80 preferably extends outwardly beyond the first end 20 of the conduit 16. In a preferred embodiment, the proximal end 84 of the wire 80 includes a conductive spherical member 90 (FIG. 1) secured thereto (e.g. integrally formed thereon). The spherical member 90 is optimally manufactured of the same material used to construct the wire 80. Use of the spherical member 90 facilitates direct contact between the wire 80 and the ear tissues of concern (e.g. the round window membrane). In an alternative embodiment (not shown), the proximal end 84 of the wire 80 may include a rounded club or hook-like portion thereon as shown in U.S. Pat. No. 5,421,818 to Arenberg instead of the spherical member 90. Thus, the proximal end 84 of the wire 80 may encompass a variety of different forms, and shall not be restricted to any single structure or design. It should likewise be noted that, while the conductive member 76 (e.g. the wire 80) is primarily discussed herein as a means to receive electrical potentials, it may also be possible to use the conductive member 76 to apply electrical potentials to tissues of interest in order to measure responsive stimuli therefrom. Thus, the conductive member 76 of the claimed invention shall not be exclusively limited to the receipt of electrical potentials.

The distal end 86 of the wire 80 preferably extends outwardly beyond the second end 22 of the fluid delivery conduit 16 as illustrated. Upon insertion of the treatment apparatus 10 into the middle ear of a patient, the distal end 86 of the wire 80 will pass through the incised tympanic membrane (or beneath a surgically formed tympanomeatal flap as described below), through the external auditory canal of the patient, and will ultimately extend outwardly from the patient's ear. The distal end 86 is then readily connected to an external monitoring apparatus 94 (FIG. 1) of conventional design which collects and characterizes resting or evoked electrical potentials ultimately received from the inner ear. Further information concerning the monitoring apparatus 94 will be presented below.

As previously noted, the conductive member 76 is especially designed to receive electrical potentials from selected inner ear tissues. This capability is particularly useful in connection with a process known as "ECoG" which is an abbreviation for "electrocochleography". Electrocochleography is a known technique for measuring electrical potentials from the inner ear which basically involves measurement of the whole nerve-cochlear action potential (hereinafter "AP"). Alternatively, ECoG can be used to indirectly measure hair cell electrical activity. ECoG can also be employed to measure the summating potential (hereinafter "SP") within the inner ear in response to externally generated clicks, tone bursts, and/or pips. The SP is basically a D.C. distortion potential which can indicate the amount of distortion in the cochlear duct associated with endolymphatic hydrops or other changes in the inner ear. The relative amount of distortion may be expressed either as an SP/AP ratio (in response to externally-generated clicks, etc.), or as an absolute measurement in response to specific, externally-generated tone bursts and the like. Cochlear microphonics can also be measured as well as otoacoustic emissions (hereinafter "OAE") in order to assess hair cell function or dysfunction. Finally, endocochlear potentials can be measured using the components described herein if selected portions of the conductive member 76 are operatively positioned within the cochlea rather than outside of the cochlea. Further information on ECoG is presented in Portmann, M., "Electrophysiological correlates of endolymphatic hypertension and endolymphatic hydrops: an overview of electrocochleography (ECoG)", Proceedings of the Third International Symposium and Workshops on the Surgery of the Inner Ear, Snowmass, Colo. (USA) Jul. 29–Aug. 4, 1990 as reported in *Inner Ear Surgery*, edited by I. Kaufman Arenberg, Kugler Publications, Amsterdam/N.Y., pp. 241–247 (1991) and in U.S. Pat. No. 5,421,818 to Arenberg which are both incorporated herein by reference. The elongate conductive member 76 may also be employed in connection with iontophoresis techniques as defined above.

As stated herein, the conductive member 76 (e.g. wire 80) is especially useful in the implementation of conventional ECoG procedures. Resting or evoked electrical potentials received by the wire 80 through direct contact of the proximal end 84 (e.g. the spherical member 90) with selected ear tissues are routed through the wire 80 to the distal end 86 which is operatively connected (using conventional electrical connecting clips and the like) to the monitoring apparatus 94 as stated above. An exemplary monitoring apparatus 94 suitable for use herein consists of commercially available ECoG detection systems sold under the names "Viking II™" and "Spirit™" by Nicolet, Inc. of Madison, Wis. (USA). However, a variety of different, commercial systems may be employed to receive and quantify electrical potentials from the conductive member 76 (e.g. wire 80), including but not limited to computer-monitored voltage amplifier/analog-to-digital converter units known in the art. As noted above, the wire 80 is sufficiently long to enable the distal end 86 thereof to terminate at a position outside of the patient's ear. As a result, attachment of the distal end 86 of the wire 80 to the monitoring apparatus 94 is greatly facilitated. In a preferred and optimum embodiment, the total length "$L_6$" (FIG. 2) of the insulated section of the wire 80 from the proximal end 84 to the distal end 86 (measured when straight) will be about 32–156 mm. Likewise, in the representative, non-limiting embodiment of FIGS. 1–2, the insulated section of the wire 80 may be divided into two portions, namely, a first portion 96 and a second portion 98. The first portion 96 (which is ultimately positioned within the fluid-receiving zone inside the round window niche as discussed below) will typically have a length "$L_7$" (FIG. 2) of about 1–15 mm. Likewise, the second portion 98 (which is ultimately located within the middle ear and external auditory canal of a patient) will normally have a length "$L_8$" (FIG. 2) of about 30–140 mm. The length of the entire wire 80 (e.g. the insulated and noninsulated sections) may be longer than the values listed above if needed, and sufficiently long to extend outwardly from the patient's ear. However, all of the above values may again be modified as necessary in accordance with a variety of factors as determined by preliminary testing on the patient of concern.

Figure 3:
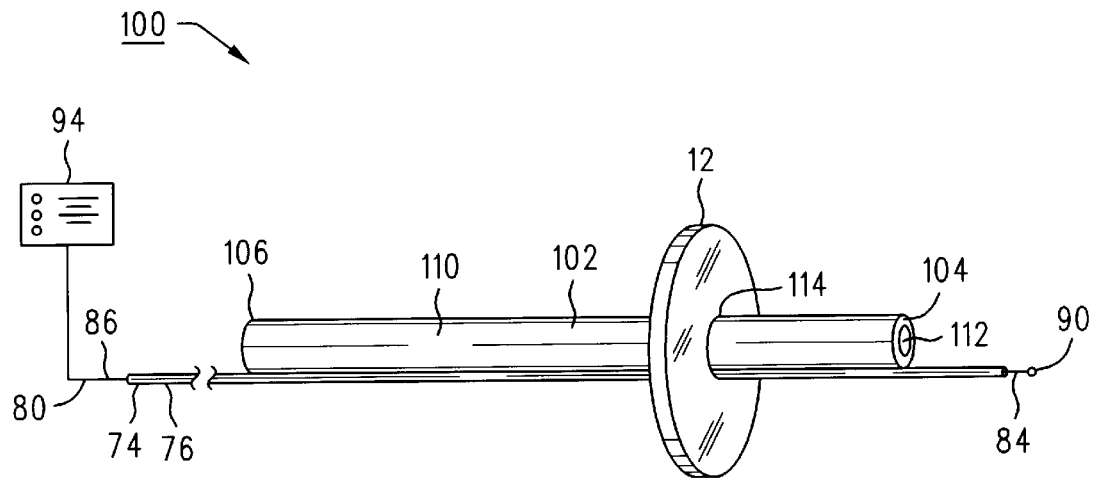
FIG. 3 is a front perspective view of a modified version of the fluid transfer and diagnostic apparatus of FIG. 1.
Figure 4:
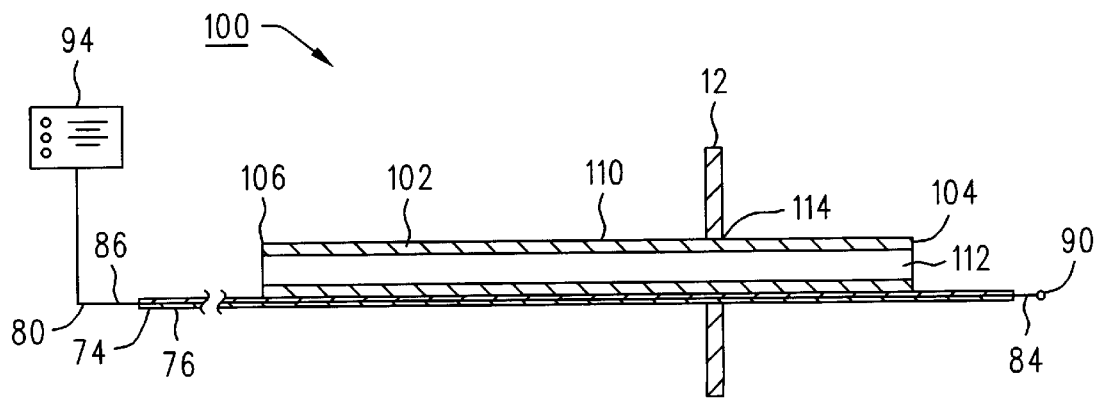
FIG. 4 is a cross-sectional view of the fluid transfer and diagnostic apparatus of FIG. 3.

Having discussed in detail the structural characteristics of treatment apparatus 10, further information regarding its use will be presented below. However, in FIGS. 3–4, a modification to apparatus 10 is illustrated at reference number 100. The use of reference numbers which are carried over from apparatus 10 (FIGS. 1–2) to apparatus 100 (FIGS. 3–4) represent components which are common to both devices. The discussion of these common components provided above in connection with the embodiment of FIGS. 1–2 shall therefore be incorporated by reference with respect to the embodiment of FIGS. 3–4. Apparatus 100 is substantially identical to apparatus 10 with one major exception, namely, the use of a single tubular conduit member instead of the dual conduits shown in FIGS. 1–2. In particular, the apparatus 100 includes a single tubular conduit 102 which is designated herein as a "fluid transfer conduit" which is operatively connected to the cover member 12. The term "operatively connected" as used in connection with the cover member 12 and fluid transfer conduit 102 shall encompass any attachment configuration which enables fluid materials to pass through both the fluid transfer conduit 102 and the cover member 12. The fluid transfer conduit 102 is designed to deliver and extract fluid materials at selected intervals from the fluid-receiving zone (e.g. the "inner ear fluid transfer space") within the round window niche as discussed above. All of the technical information, size parameters, and the like which were provided above regarding the fluid delivery conduit 16 (and attachment of the electrical potential transmission means 74 thereto) are equally applicable to the fluid transfer conduit 102. For example, like the fluid delivery conduit 16, the fluid transfer conduit 102 includes an open first end 104, an open second end 106, and a medial portion 110 therebetween. In addition, the fluid transfer conduit 102 includes a central passageway 112 therein which extends continuously through the conduit 102 from the first end 104 to the second end 106. The conduit 102 likewise passes through an opening 114 in the cover member 12 (FIG. 3) which is optimally the same size as the opening 34 in the embodiment of FIGS. 1–2. Once again, all of the other features, components, parameters, and dimensions associated with the apparatus 100 of FIGS. 3–4 are the same as those described above in connection with the apparatus 10. In addition, the term "operatively connected" as used in connection with the cover member 12 and the fluid transfer conduit 102 shall include placement of the first end 104 of the fluid transfer conduit 102 flush with the opening 114 through the cover member 12 so that no part of the first end 104 actually extends outward from the cover member 12.

The apparatus 100 of FIGS. 3–4 is designed for situations in which it is not required (as determined by preliminary experimental testing and/or clinical analysis) to have a separate conduit for fluid delivery and fluid extraction. Thus, when it is necessary to introduce fluid materials (e.g. therapeutic fluid compositions as noted above) into the fluid-receiving zone (round window niche) using the apparatus 100, this step can be accomplished using the fluid transfer conduit 102. When fluid materials (e.g. "residual" therapeutic agents, inner ear tissue fluids, and the like) are to be withdrawn from the fluid-receiving zone, such materials can likewise be removed using the fluid transfer conduit 102. This embodiment is particularly useful in situations where the round window membrane is to be repeatedly washed or "flushed" with a selected therapeutic fluid, followed by rapid removal of the fluid in a successive manner using a single suction/delivery apparatus (e.g. a syringe, pump apparatus, and the like). Further information concerning this particular embodiment will be presented below in the "Methods of Use" section.

Figure 5:
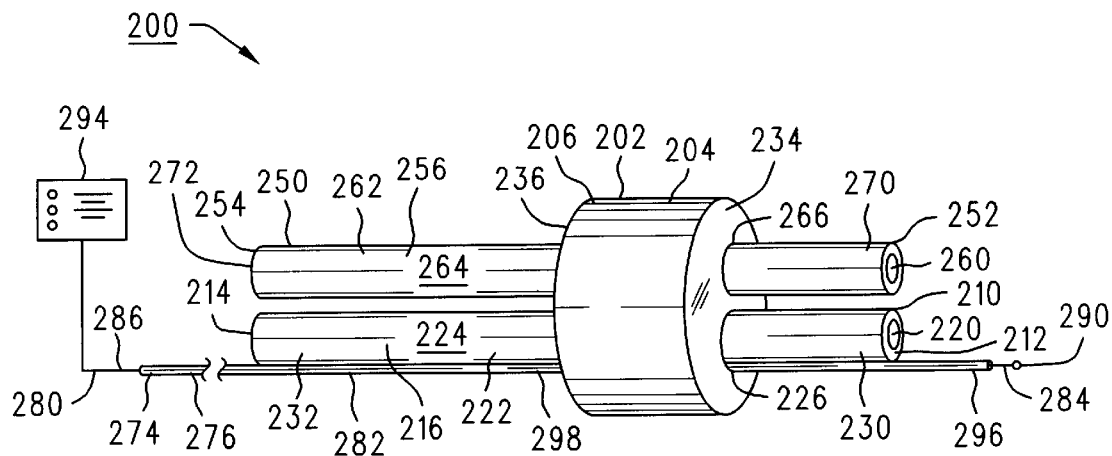
FIG. 5 is a front perspective view of a secondary embodiment of the claimed fluid transfer and diagnostic apparatus.
Figure 6:
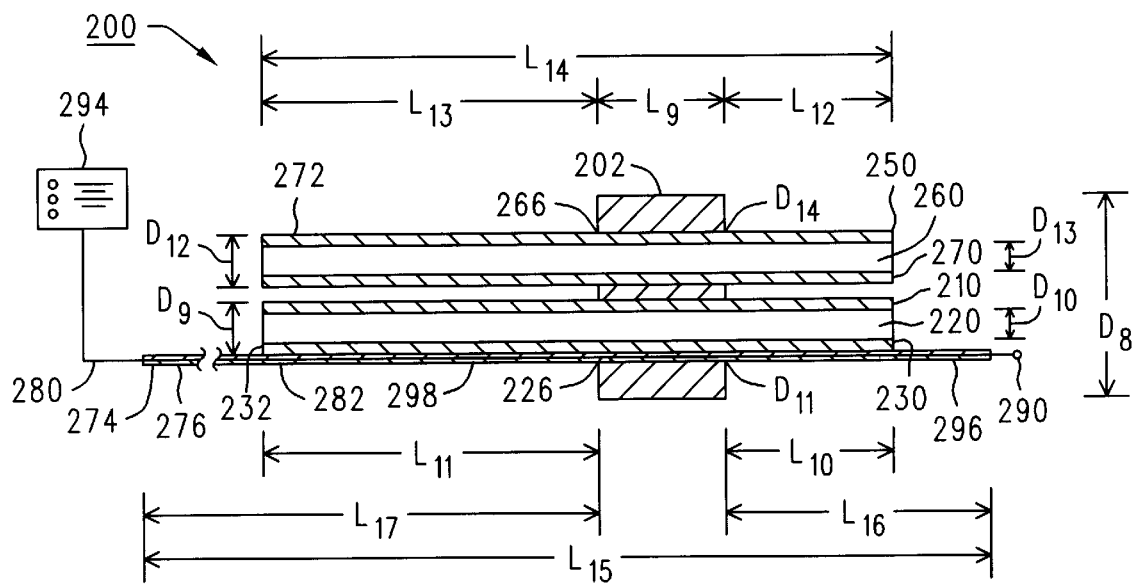
FIG. 6 is a cross-sectional view of the fluid transfer and diagnostic apparatus of FIG. 5.

A further variation of the claimed invention is illustrated schematically and in enlarged format in FIGS. 5–6. While the main goals to be accomplished using this embodiment are the same as those discussed above (e.g. the formation of a sealed fluid-receiving zone or "inner ear fluid transfer space" within the round window niche), such goals are accomplished using different components. With reference to FIGS. 5–6, an alternative treatment apparatus is shown at reference number 200. Apparatus 200 uses a different type of cover member 202 which will now be discussed in detail. With continued reference to FIGS. 5–6, the cover member 202 consists of a body portion 204 which is dissimilar to the flat, plate-like body portion 14 employed as the cover member 12 in the first embodiment discussed above. Specifically, the cover member 202 involves a plug-like portion of compressible material 206 (FIG. 5) which, during placement within the round window niche, is manually compressed by the treating physician and thereafter allowed to expand once the portion of compressible material 206 is positioned within the round window niche. As a result, the cover member 202 can engage the interior side wall of the round window niche and provide a fluid-tight seal within the niche. The fluid-tight seal forms a sealed fluid-receiving zone between the cover member (the upper boundary of the fluid-receiving zone) and the round window membrane (the lower boundary of the zone). This process will be outlined in greater detail below (along with appropriate drawing figures) in the "Methods of Use" section.

Many different materials may be used to produce the cover member 202, with the present invention not being restricted to any particular compositions for this purpose. However, the selected construction materials to be employed in connection with the cover member 202 must be highly flexible, resilient, biologically-inert, compressible, and non-fluid absorbent in order to avoid the absorption of fluid materials (e.g. medicines) directly into the body portion 204 of the cover member 202. Likewise, it is preferred that the selected composition be sufficiently compressible to enable the cover member 202 to be reduced in size (volume) during compression by at least 50–75% compared with its original volume. Representative materials which may be used to construct the portion of compressible material associated with the cover member 202 in this alternative embodiment include but are not limited to polyethylene foam, polyether foam, polyester form, polyvinyl chloride foam, polyurethane foam, and sponge rubber (e.g. synthetic or natural), all of which are of the closed cell variety, with such materials being non-fluid-absorbent in accordance with the substantial lack of open cells therein. Specifically, the non-fluid absorbent character of these materials results from the closed cell character thereof which prevents fluid materials from being absorbed compared with open cell (absorbent) foam products. Likewise, in a preferred embodiment using the compositions listed above, the body portion 204 of the cover member 202 will be sized so that, when compressed, it will not occupy the entire volume of the round window niche, thereby leaving sufficient space for the fluid-receiving zone therein. As shown in FIGS. 5–6, this may be accomplished by using a cover member 202 which is substantially circular in cross-section with a uniform E length "$L_9$" (FIG. 6) of about 3.0–7.0 mm and a uniform diameter "$D_8$" (FIG. 6) of about 2.0–8.0 mm. After compression of the cover member 202 within the round window niche of a typical patient, it is anticipated that diameter "$D_8$" will be reduced by approximately 50–75%. However, the claimed invention shall not be restricted to these dimensions which may be varied as needed and determined by clinical investigations. Likewise, it is important to note that the overall configuration (e.g. size and shape) of the cover member 202 may be custom-manufactured to the particular contours and size characteristics of a specific patient's round window niche if needed and desired. For example, custom manufacturing and production of a suitably-sized cover member 202 may be appropriate in situations where the patient of concern is a small child.

The other components of the treatment apparatus 200 will now be discussed. As illustrated in FIGS. 5–6, the apparatus 200 further includes at least one fluid delivery conduit 210 operatively connected (e.g. attached) thereto. The fluid delivery conduit 210 is specifically used in this embodiment to introduce selected fluid (e.g. liquid) materials including therapeutic fluid compositions into the fluid-receiving zone through the cover member 200. The fluid delivery conduit 210 includes an open first end 212, an open second end 214, and a medial portion 216 between the first and second ends 212, 214 (FIG. 5). In addition, the fluid delivery conduit 210 is tubular in construction, with the term "tubular" again being defined to encompass a structure which includes a continuous central passageway therethrough that is surrounded by an outer wall. As illustrated in FIGS. 5–6, a central passageway 220 is provided which extends continuously through the conduit 210 from the first end 212 to the second end 214. Surrounding the central passageway 220 is a side wall 222 having an outer surface 224 (FIG. 5).

The fluid delivery conduit 210 is optimally circular in cross-section with a uniform external diameter "$D_9$" (FIG. 6) of about 0.5–2.0 mm. Likewise, in a preferred embodiment, the passageway 220 through the conduit 210 will have a uniform internal diameter "D10" (FIG. 6) of about 0.1–0.6 mm which is sufficient to allow the passage of therapeutic fluid compositions and other fluid materials therethrough. Representative biologically-inert construction materials which may be employed to produce the fluid delivery conduit 210 are the same as those listed above in connection with the fluid delivery conduit 16. Silicone rubber, latex rubber, and plastic can be employed for this purpose. The term "plastic" as used herein shall again encompass a wide variety of compositions including but not limited to polycarbonate, polyester, polyethylene, polypropylene, polyvinyl chloride, nylon, cellophane, and other comparable materials. It should be noted that this embodiment of the present invention shall not be restricted to any specific dimensions, construction materials, and other parameters relative to the fluid delivery conduit 210. All of these parameters may be determined in accordance with a variety of considerations including the intended use of the apparatus 200 and the specific otological conditions being treated.

With continued reference to FIGS. 5–6, the fluid delivery conduit 210 is operatively connected to the cover member 202 as illustrated. The term "operatively connected" as used in connection with the cover member 202 and fluid delivery conduit 210 shall encompass any attachment configuration which enables fluid materials to pass through both the fluid delivery conduit 210 and the cover member 202. In the embodiment of FIGS. 5–6, the fluid delivery conduit 210 passes through the cover member 202 in a fluid-tight manner with the first end 212 of the conduit 210 being on one side of the cover member 202 and the second end 214 of the conduit 210 being on the other side. This is specifically accomplished by providing a first opening 226 through the cover member 202 as illustrated. In a preferred embodiment, the first opening 226 will have a diameter "$D_{11}$" (FIG. 6) that is about 5–10% smaller than the external diameter "$D_9$" of the fluid delivery conduit 210 so that the conduit 210 may be tightly and securely engaged within the opening 226 (which is readily accomplished in accordance with the resilient character of the materials used to produce the cover member 202). In this regard, the diameter "$D_{11}$" of the first opening 226 will be about 0.45–1.9 mm in a representative, non-limiting embodiment.

Attachment of the fluid delivery conduit 210 to the cover member 202 is specifically accomplished by passing the first end 212 of the conduit 210 through the opening 226 in the cover member 202 until the medial portion 216 of the conduit 210 is securely engaged therein. The conduit 210 (e.g. the medial portion 216) may be maintained within the opening 226 by frictional engagement between these components or the use of a variety of conventional adhesive materials including epoxy resin and/or cyanoacrylate adhesives known in the art. Regarding frictional engagement of the conduit 210 within the opening 226, it is important to note that such engagement will be enhanced and increased when the body portion 204 of the cover member 202 is compressed during placement of the cover member 202 within the round window niche of a patient as discussed in detail below. It should also be noted that the term "operatively connected" as used in connection with the cover member 202 and the fluid delivery conduit 210 may likewise include placement of the first end 212 of the fluid delivery conduit 210 flush with the opening 226 through the cover member 202 or inside the cover member 202 so that no part of the first end 212 actually extends outwardly from the cover member 202.

However, in the system of FIGS. 5–6, the fluid delivery conduit 210 (after connection to the cover member 202) is divided into a primary section 230 and a secondary section 232. In a representative and non-limiting embodiment, the primary section 230 (and the first end 212) of the conduit 210 extends outwardly from the inner end 234 of the cover member 202. As a result, during use of the apparatus 200, the primary section 230 and first end 212 will be entirely located within the round window niche of the patient being treated. Likewise, to achieve proper use of the apparatus 200, the primary section 230 of the fluid delivery conduit 210 will have a representative length "$L_{10}$" (FIG. 6) of about 10–80 mm although this value may be varied as needed and desired. The conduit 210 will also include a secondary section 232 as previously noted which (along with the second end 214 of the conduit 210) extends outwardly from the outer end 236 of the cover member 202. During use of the apparatus 10, the secondary section 232 and second end 214 of the conduit 210 will be located entirely outside of the round window niche and at least partially within the external auditory canal of the patient. To achieve proper use of the apparatus 200, the secondary section 232 will have a representative length "$L_{11}$" (FIG. 6) of about 20–150 mm although this value may be varied as needed and desired.

The basic purpose of the fluid delivery conduit 210 is to enable fluid materials (e.g. liquid drugs or other therapeutic fluid compositions) to be passed through the cover member 202 for ultimate delivery into the fluid-receiving zone ("inner ear fluid transfer space") inside the round window niche. These materials can thereafter pass by diffusion, osmosis, and the like into the inner ear via the round window membrane. However, in the apparatus 200 of FIGS. 5–6, a separate conduit member is provided which may be used to withdraw various fluid materials (e.g. "residual" compositions) from the fluid-receiving zone during or after transfer of the therapeutic fluid compositions into the zone by the fluid delivery conduit 210. Fluid materials which may be withdrawn from the fluid-receiving zone by this additional conduit include but are not limited to residual therapeutic agents and various inner ear fluids that have diffused through the round window membrane. To accomplish this goal, a separate fluid extraction conduit 250 is provided adjacent the fluid delivery conduit 210. Both of the conduits 210, 250 will preferably be identical in every respect including size/length parameters and construction materials. However, to provide a full and complete disclosure of the current embodiment, a detailed discussion of the fluid extraction conduit 250 will now be presented.

As previously indicated, the fluid extraction conduit 250 is specifically used to remove selected fluid (e.g. liquid) materials from the fluid-receiving zone through the cover member 202. The fluid extraction conduit 250 includes an open first end 252, an open second end 254, and a medial portion 256 between the first and second ends 252, 254 (FIG. 5). In addition, the fluid extraction conduit 250 is tubular in construction, with the term "tubular" being defined above. As illustrated specifically in FIGS. 5–6, a central passageway 260 is provided within the conduit 250 which extends continuously through the conduit 250 from the first end 252 to the second end 254. Surrounding the central passageway 260 is a side wall 262 having an outer surface 264 (FIG. 5).

The fluid extraction conduit 250 is optimally circular in cross-section with a uniform external diameter "$D_{12}$" (FIG. 6) of 0.5–2.0 mm. Likewise, in a preferred embodiment, the passageway 260 through the conduit 250 will have a uniform internal diameter "$D_{13}$" (FIG. 6) of about 0.1–0.6 mm which is sufficient to allow the passage of fluid materials therethrough. Representative biologically-inert construction materials which may be employed to produce the fluid extraction conduit 250 comprise the same materials listed above in connection with the fluid delivery conduit 210 and the fluid extraction conduit 50 in the embodiment of FIGS. 1–2, namely, silicone rubber, latex rubber, and plastic. The term "plastic" as used herein shall again encompass a wide variety of compositions including but not limited to polycarbonate, polyester, polyethylene, polypropylene, polyvinyl chloride, nylon, cellophane, and other comparable materials.

With continued reference to FIGS. 5–6, the fluid extraction conduit 250 is operatively connected to the cover member 202 as illustrated. The term "operatively connected" as used in connection with the cover member 202 and fluid extraction conduit 250 shall encompass any attachment configuration which enables fluid materials to pass through both the fluid extraction conduit 250 and the cover member 202. In the embodiment of FIGS. 1–2, the fluid extraction conduit 250 passes through the cover member 202 in a fluid-tight manner with the first end 252 of the conduit 250 being on one side of the cover member 202 and the second end 254 of the conduit 250 being on the other side. This is accomplished by providing a second opening 266 through the cover member 202 as illustrated. In a preferred embodiment, the second opening 266 will have a diameter "$D_{14}$" (FIG. 6) that is about 5–10% smaller than the external diameter "$D_{12}$" of the fluid extraction conduit 250 so that the conduit 250 may be tightly and securely engaged within the opening 266 (which is readily accomplished in accordance with the resilient character of the materials used to produce the cover member 202). In this regard, the diameter "$D_{14}$" of the second opening 266 will be about 0.45–1.9 mm in a representative, non-limiting embodiment.

Attachment of the fluid extraction conduit 250 to the cover member 202 is specifically accomplished by passing the first end 252 of the conduit 250 through the opening 266 in the cover member 202 until the medial portion 256 of the conduit 250 is securely engaged therein. The conduit 250 (e.g. the medial portion 256) may be maintained within the opening 266 by frictional engagement between these components or through the use of a variety of conventional adhesive materials including epoxy resin and/or cyanoacrylate adhesives known in the art. Regarding frictional engagement of the conduit 250 within the opening 266, it is important to note that such engagement will be enhanced and increased when the body portion 204 of the cover member 202 is compressed during placement of the cover member 202 in the round window niche of a patient. Furthermore, it is also contemplated that, instead of providing the second opening 266, the fluid extraction conduit 250 may be passed through the first opening 226 along with the fluid delivery conduit 210, with the first opening 226 being suitably enlarged for this purpose. In such a system, the first opening 226 would have an enlarged diameter "$D_{11}$" (FIG. 6) of about 0.9–3.8 mm to accommodate both of the conduits 210, 250 therein. While it is preferred that the present embodiment incorporate dual openings 226, 266 for each of the conduits 210, 250, the claimed apparatus 200 shall not be restricted to any particular construction methods or design configurations. It should also be noted that the term "operatively connected" as used in connection with the cover member 202 and the fluid extraction conduit 250 may likewise include placement of the first end 252 of the fluid extraction conduit 250 flush with the opening 266 through the cover member 202 or inside the cover member 202 so that no part of the first end 252 actually extends outwardly from the cover member 202.

As shown in FIGS. 5–6, the fluid extraction conduit 250 (after connection to the cover member 202) is divided into a primary section 270 and a secondary section 272. The primary section 270 (and the first end 252) extend outwardly from the inner end 234 of the cover member 202. As a result, during use of the apparatus 200, the primary section 270 and first end 252 will be entirely located within the round window niche of the patient being treated. Likewise, to achieve proper use of the apparatus 200, the primary section 270 of the fluid delivery conduit 250 will have a length "$L_{12}$" (FIG. 6) of about 10–80 mm which is substantially equal to the length "$L_{10}$" (FIG. 6) of the primary section 230 of the conduit 210 discussed above, although this value may be varied as needed and desired. The conduit 250 will also include a secondary section 272 which (along with the second end 254 of the conduit 250) extends outwardly from the outer surface 236 of the cover member 202. As a result, during use of the apparatus 200, the secondary section 272 and second end 254 of the conduit 250 will be located entirely outside of the round window niche and at least partially within the external auditory canal of the patient. To achieve proper use of the apparatus 200, the secondary section 272 will have a length "$L_{13}$" (FIG. 6) of about 20–150 mm which is substantially equal to the length "$L_{11}$" (FIG. 6) of the secondary section 232 of the conduit 210 discussed above, although this value may be varied as needed and desired.

The completed treatment apparatus 200 is illustrated in FIGS. 5–6 and, in a preferred, non-limiting embodiment, will have an overall length "$L_{14}$" (FIG. 6) of about 33–237 mm. Use of the apparatus 200 will be discussed below in the "Methods of Use" section. However, at this time, it is important to note that the apparatus 200 and its use of dual (separate) fluid delivery and fluid extraction conduits 210, 250 is designed to avoid cross-contamination of the fluid materials being delivered and/or extracted from the fluid-receiving zone within the round window niche of the patient. This goal is important when precise amounts of therapeutic agents (e.g. microgram/nanogram/nanoliter quantities) are to be delivered in a highly controlled manner. Having dual fluid delivery and extraction conduits 210, 250 specifically enables the entire treatment process to be more carefully monitored, controlled, and assessed.

Finally, as shown in FIGS. 5–6, another feature of the apparatus 200 is illustrated. This feature, while optional in nature, provides many important benefits. The treatment apparatus 200 of FIGS. 5–6 includes electrical potential transmission means 274 fixedly secured to the fluid delivery conduit 210 for receiving evoked or non-evoked electrical potentials from middle/inner ear tissues and transmitting them out of the ear for the detection and analysis thereof. While the electrical potential transmission means 274 is shown attached to the fluid delivery conduit 210, it is important to note that the electrical potential transmission means 274 may be operatively connected to at least one of the fluid delivery conduit 210 and the fluid extraction conduit 250. The components associated with the electrical potential transmission means 274 (discussed below) may specifically be connected to (A) the fluid delivery conduit 210; (B) the fluid extraction conduit 250; or (C) both of the conduits 210, 250. However, for the sake of clarity, the following discussion shall involve attachment of the electrical potential transmission means 274 to the fluid delivery conduit 210, with all of the information provided below being equally applicable to connection of the electrical potential transmission means 274 to the fluid extraction conduit 250.

The electrical potential transmission means 274 in the embodiment of FIGS. 5–6 is substantially the same as the electrical potential transmission means 74 in the embodiment of FIGS. 1–2. Thus, all of the information provided above regarding the electrical potential transmission means 74 is incorporated by reference in connection with the electrical potential transmission means 274 in the embodiment of FIGS. 5–6. However, such information will now be summarized in order to provide a full and complete disclosure. As illustrated in FIGS. 5–6, the electrical potential transmission means 274 consists of an elongate conductive member 276 fixedly secured to the fluid delivery conduit 210 along the entire length of the conduit 210. It specifically passes through the first opening 226 in the cover member 202 along with the medial portion 216 of the conduit 210. The size parameters listed above in connection with the first opening 226 should be sufficient to accommodate passage of both the fluid delivery conduit 210 and the elongate conductive member 276 therethrough. The elongate conductive member 276 may involve a variety of different structures. For example, it is preferred that the conductive member 276 again consist of a thin wire 280 (e.g. #27 gauge) manufactured from titanium. The wire 280 is preferably coated with a layer 282 of insulation thereon (FIGS. 5–6). Representative insulation materials which may be used for this purpose include but are not limited to heat shrinkable Teflon® (polytetrafluoroethylene) tubing of a type well known in the art. The wire 280 (conductive member 276) further includes a proximal end 284 and a distal end 286 as illustrated (FIG. 5). The wire 280 (surrounded by the layer 282 of insulation) is fixedly secured to the fluid delivery conduit 210 of the apparatus 200 in any desired or suitable position thereon. In the embodiment of FIGS. 5–6, the wire 280 is secured to the conduit 210 of the apparatus 200 along the underside of the conduit 210. Attachment may be accomplished using a medical grade adhesive of the type set forth above (e.g. cyanoacrylate, epoxy resin, or other conventional adhesive materials). The term "secured" or "attached" as used in connection with the electrical potential transmission means 274/conductive member 276 can also encompass a situation in which this component is directly incorporated (e.g. molded) into the side walls 222, 262 of one or both of the fluid delivery and fluid extraction conduits 210, 250. It should also be noted that the conductive member 276 may involve other structures equivalent to the wire 280. For example, a substantially flat, flexible metallic strip (not shown) may be used in place of the wire 280, although the wire 280 is preferred.

As shown in FIGS. 5–6, the wire 280 preferably extends outwardly beyond the first end 212 of the conduit 210. In a preferred embodiment, the proximal end 284 of the wire 280 includes a conductive spherical member 290 secured thereto (e.g. integrally formed thereon). The spherical member 290 is optimally manufactured of the same material used to construct the wire 280. Use of the spherical member 290 facilitates direct contact between the wire 280 and the ear tissues of concern (e.g. the round window membrane). In an alternative embodiment (not shown), the proximal end 284 of the wire 280 may include a rounded club or hook-like portion thereon instead of the spherical member 290 as further discussed and illustrated in U.S. Pat. No. 5,421,818 to Arenberg. The proximal end 284 of the wire 280 may therefore encompass a variety of different forms, and shall not be limited to any single structure or design. In addition, while the conductive member 276 (e.g. the wire 280) is primarily discussed herein as a means to receive electrical potentials, it may also be possible to use the conductive member 276 to apply electrical potentials to tissues of interest in order to measure responsive stimuli therefrom. Thus, the conductive member 276 of the apparatus 200 shall not be exclusively limited to the receipt of electrical potentials and shall also be applicable to a variety of other techniques including iontophoresis as defined above.

The distal end 286 of the wire 280 (conductive member 276) preferably extends outwardly beyond the second end 214 of the fluid delivery conduit 210 as shown. Upon insertion of the treatment apparatus 200 into the middle ear of a patient, the distal end 286 of the wire 280 will pass through the incised tympanic membrane (or beneath a surgically formed tympanomeatal flap as described below), through the external auditory canal of the patient, and will ultimately extend outwardly from the patient's ear. The distal end 286 is then readily connected to an external monitoring apparatus 294 (FIGS. 5–6) of conventional design which collects and characterizes resting or evoked electrical potentials ultimately received from the inner ear. Further information concerning the monitoring apparatus 294 will be described below.

As indicated herein, the conductive member 276 is especially designed to receive electrical potentials from selected inner ear tissues. This capability is particularly useful in connection with ECoG procedures as discussed in substantial detail above. Likewise, as previously noted, further information on ECoG is presented in Portmann, M., "Electrophysiological correlates of endolymphatic hypertension and endolymphatic hydrops: an overview of electrocochleography (ECoG)", Proceedings of the Third International Symposium and Workshops on the Surgery of the Inner Ear, Snowmass, Colo. (USA) Jul. 29–Aug. 4, 1990 as reported in *Inner Ear Surgery*, edited by I. Kaufman Arenberg, Kugler Publications, Amsterdam/N.Y., pp. 241–247 (1991) and in U.S. Pat. No. 5,421,818 to Arenberg which are both incorporated herein by reference.

Resting or evoked electrical potentials received by the wire 280 through direct contact of the proximal end 284 (e.g. the spherical member 290) with selected ear tissues are routed through the wire 280 to the distal end 286 which is operatively connected (using conventional electrical connecting clips and the like) to the monitoring apparatus 294. An exemplary monitoring apparatus 294 suitable for use herein will involve the same system listed above in connection with the monitoring apparatus 94. In particular, a representative monitoring apparatus 294 appropriate for use in the embodiment of FIGS. 5–6 consists of commercially available ECoG detection systems sold under the names "Viking II™" and "Spirit™" by Nicolet, Inc. of Madison, Wis. (USA). However, a variety of different commercial systems may be employed to receive and quantify electrical potentials from the conductive member 276 (e.g. wire 280), including but not limited to computer-monitored voltage amplifier/analog-to-digital converter units known in the art. The wire 280 is sufficiently long to enable the distal end 286 thereof to terminate at a position outside of the patient's ear as previously noted. In this manner, attachment of the distal end 286 of the wire 280 to the monitoring apparatus 294 is greatly facilitated. In a preferred and optimum embodiment, the total length "$L_{15}$" (FIG. 6) of the insulated portion of the wire 280 from the proximal end 284 to the distal end 286 (measured when straight) will be about 34–162 mm. Likewise, in the representative, non-limiting system of FIGS. 5–6, the insulated section of the wire 280 may be divided into two portions, namely, a first portion 296 and a second portion 298. The first portion 296 (which is ultimately positioned within the fluid-receiving zone inside the round window niche as discussed below) will typically have a length "$L_{16}$" (FIG. 6) of about 1–15 mm. Likewise, the second portion 298 (which is ultimately positioned within the middle ear and external auditory canal of a patient) will normally have a length "$L_{17}$" of about 30–140 mm. The length of the entire wire 280 (e.g. the insulated and non-insulated sections) may be longer than the values listed above if needed, and sufficiently long to extend outwardly from the patient's ear. However, all of the above values may be modified as necessary in accordance with a variety of factors as determined by preliminary testing on the patient of concern.

Figure 7:
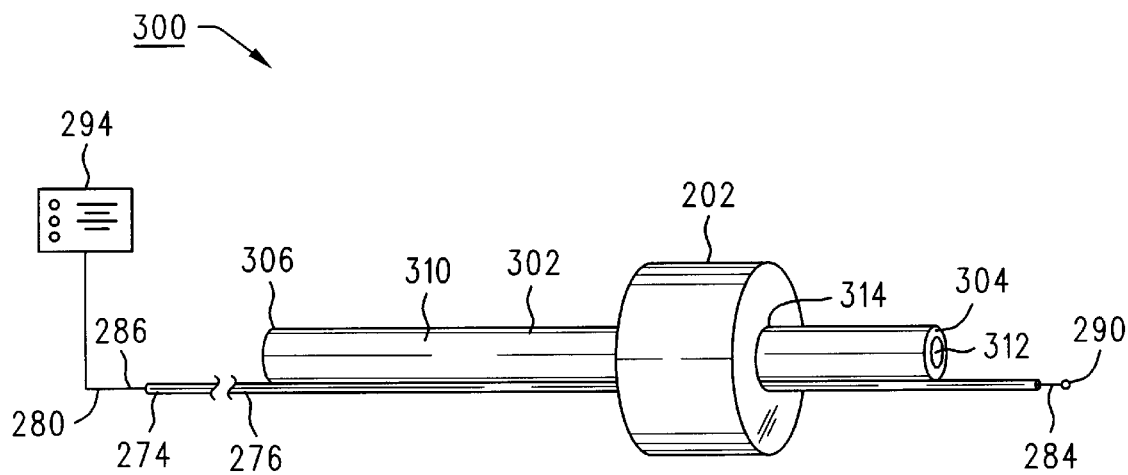
FIG. 7 is a front view perspective view of a modified version of the fluid transfer and diagnostic apparatus of FIG. 5.
Figure 8:
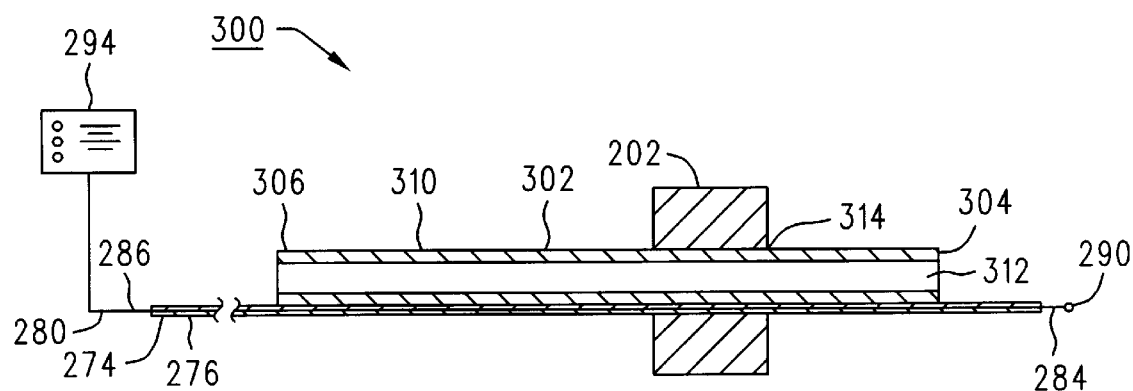
FIG. 8 is a cross-sectional view of the fluid transfer and diagnostic apparatus of FIG. 7.

Having discussed in detail the structural characteristics of treatment apparatus 200, further information regarding its use will be presented below. However, in FIGS. 7–8, a modification to apparatus 200 is shown at reference number 300. The use of reference numbers which are carried over from apparatus 200 (FIGS. 5–6) to apparatus 300 (FIGS. 7–8) represent components which are common to both devices. The discussion of these common elements in connection with the embodiment of FIGS. 5–6 as provided above shall therefore be incorporated by reference with respect to the embodiment of FIGS. 7–8. Apparatus 300 is substantially identical to apparatus 200 with one major exception, namely, the use of a single tubular conduit instead of the dual conduits shown in FIGS. 5–6. In particular, the apparatus 300 includes a single tubular conduit 302 which is designated herein as a "fluid transfer conduit" and is operatively connected to the cover member 202. The term "operatively connected" as used in connection with the cover member 202 and fluid transfer conduit 302 shall encompass any attachment configuration which enables fluid materials to pass through both the fluid transfer conduit 302 and the cover member 202. The fluid transfer conduit 302 is designed to deliver and extract fluid materials at selected intervals from the fluid-receiving zone within the round window niche. All of the technical information, parameters, dimensions, definitions, and the like which were provided above regarding the fluid delivery conduit 210 (and attachment of the electrical potential transmission means 274 thereto) are equally applicable to the fluid transfer conduit 302. For example, the fluid transfer conduit 302 includes an open first end 304, an open second end 306, and a medial portion 310 therebetween. In addition, the fluid transfer conduit 302 includes a central passageway 312 therein which extends continuously through the conduit 302 from the first end 304 to the second end 306. The conduit 302 likewise passes through an opening 314 in the cover member 202 which is optimally the same size as the opening 226 in the embodiment of FIGS. 5–6. Once again, all of the other features, components, parameters, and dimensions associated with the apparatus 300 of FIGS. 7–8 are the same as those described above in connection with the apparatus 200. It should also be noted that the term "operatively connected" as used in connection with the cover member 202 and the fluid transfer conduit 302 may likewise include placement of the first end 304 of the fluid transfer conduit 302 flush with the opening 314 through the cover member 202 or inside the cover member 202 so that no part of the first end 304 actually extends outwardly from the cover member 202.

The apparatus of FIGS. 7–8 is designed for situations in which it is not necessary (as determined by preliminary experimental testing and clinical evaluations) to have a separate conduit for fluid delivery and fluid extraction. Thus, when fluid materials are to be introduced into the fluid-receiving zone, this step can be accomplished using the fluid transfer conduit 302. Likewise, when fluid materials ("residual" therapeutic agents, inner ear tissue fluids, and the like) are to be withdrawn from the fluid-receiving zone, such materials can also be removed using the fluid transfer conduit 302. This embodiment is particularly useful in situations where the round window membrane is to be repeatedly washed (e.g. "flushed") with a selected therapeutic fluid, followed by rapid removal of the fluid in a successive manner using a single suction/delivery apparatus (e.g. a syringe, pump apparatus, and the like). Further information concerning this variation of the present invention will be presented below in the "Methods of Use" section.

Having presented detailed information regarding the various structural embodiments of the claimed apparatus, additional information will now be provided involving the manner in which these embodiments may be used to transfer fluid materials into and out of the inner ear of a human subject.

B. Methods of Use

Figure 9:
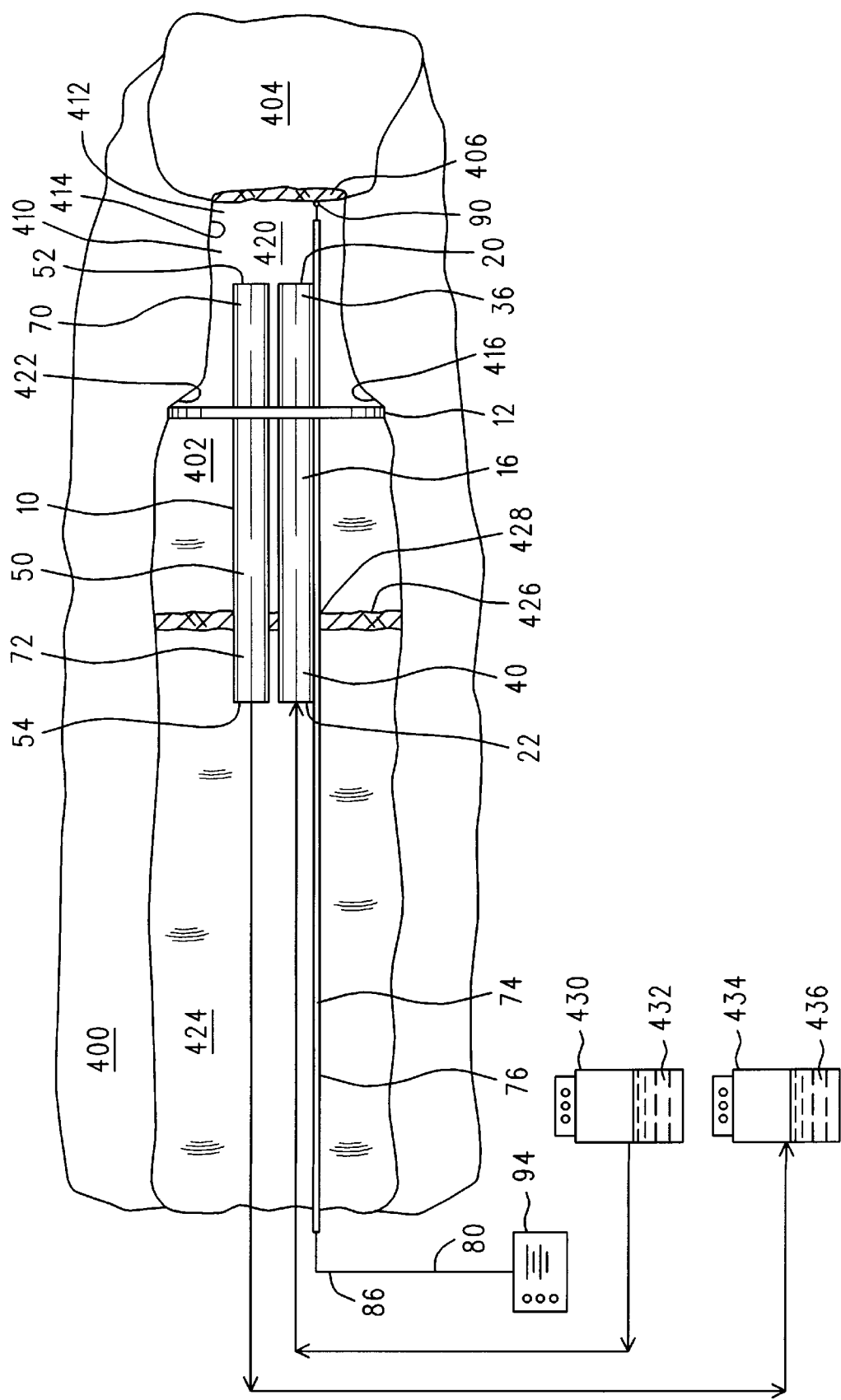
FIG. 9 is a schematic representation of the fluid transfer and diagnostic apparatus of FIG. 1 positioned within the ear of a human subject, with the same representation being applicable to the embodiment of FIG. 3.
Figure 10:
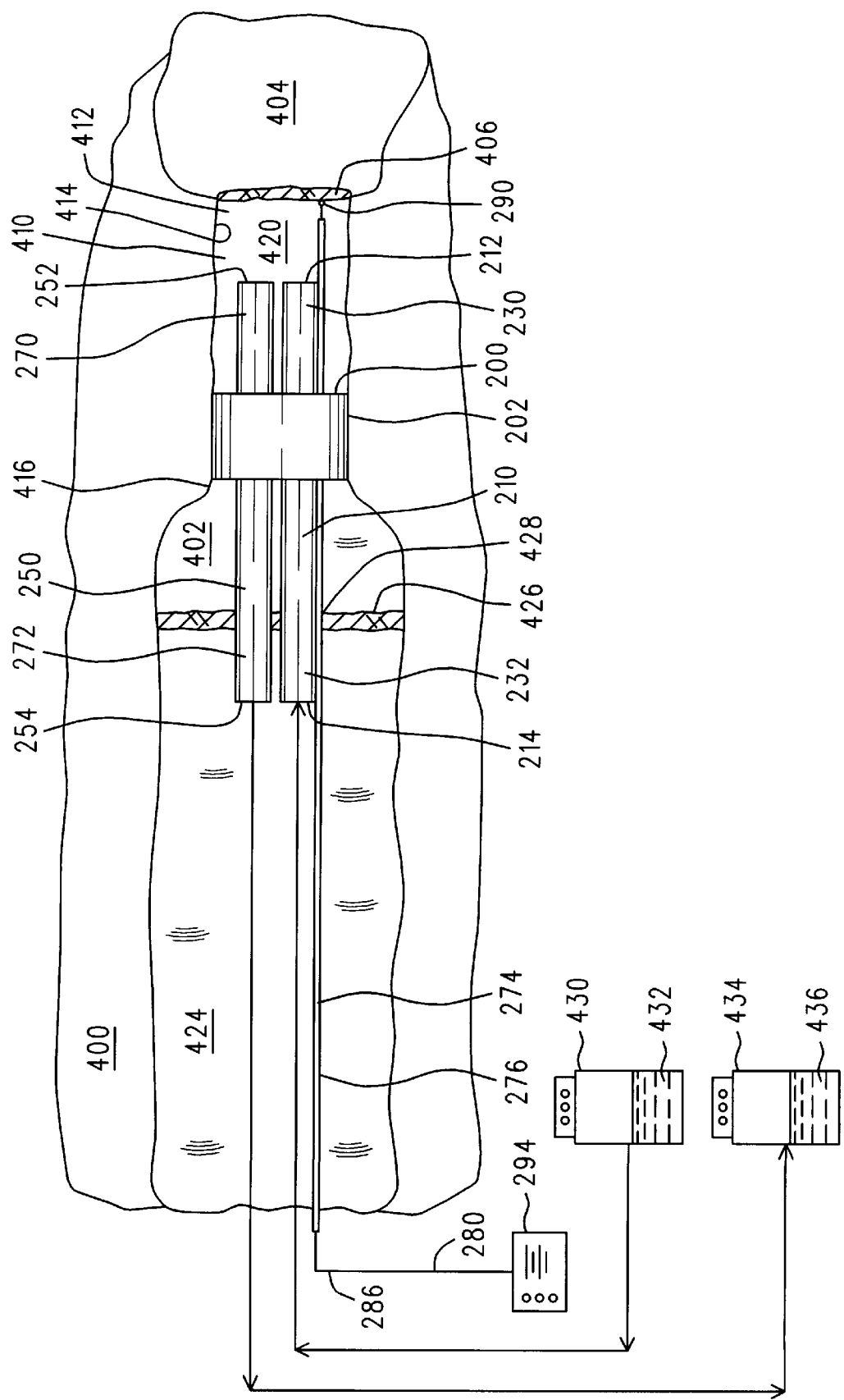
FIG. 10 is a schematic representation of the fluid transfer and diagnostic apparatus of FIG. 5 positioned within the ear of a human subject, with the same representation being applicable to the embodiment of FIG. 7.

Methods for using the devices associated with the claimed fluid transfer and diagnostic systems will now be discussed. The present invention shall not be restricted to any particular surgical methods for introducing the devices of the invention into a patient's ear, with many different techniques being suitable for this purpose provided that, in some manner, the fluid receiving zone ("inner ear fluid transfer space") of the invention is effectively created. Likewise, the structures of the human ear illustrated in FIGS. 9–10 are schematic in nature and enlarged for the sake of clarity. More detailed information regarding these structures is provided in U.S. Pat. No. 5,421,818 which is incorporated herein by reference.

FIG. 9 is a schematic, partial cross-sectional view of the ear 400 of a human subject illustrating the treatment apparatus 10 of FIG. 1 inserted therein. As shown in FIG. 9, the apparatus 10 is positioned so that the cover member 12 is entirely located within the middle ear, generally designated in FIG. 9 at reference number 402. The inner ear is shown at reference number 404, with the specific components of the inner ear 404 (including the cochlea, the endolymphatic sac, as well as the endolymphatic duct being omitted for the sake of clarity and illustrated in U.S. Pat. No. 5,421,818). The round window membrane is generally designated at reference number 406, and constitutes an interface tissue structure between the middle ear 402 and the inner ear 404. Likewise, the round window niche is shown at reference number 410 (which basically consists of an internal cavity 412), with the round window niche 410 further including an interior side wall 414 and a main opening 416 leading into the internal cavity 412/round window niche 410.

The first step in using the apparatus 10 involves insertion of the cover member 12 within the middle ear 402 as illustrated. The cover member 12 is then placed on and over the main opening 416 which leads into the round window niche 410. As previously noted, the cover member 12 is sized to completely cover the main opening 416 in order to seal the main opening 416 (e.g. the internal cavity 412) so that a sealed fluid-receiving zone 420 or "inner ear fluid transfer space" is created (FIG. 9). The fluid receiving zone 420 is bounded by (1) the cover member 12 which forms an upper or external boundary; and (2) the round window membrane 406 which forms a lower or internal boundary.

The cover member 12 may be maintained in position adjacent and against the main opening 416 leading into the round window niche 410 using many different methods, with the present invention not being limited to any particular technique for this purpose. For example, to create a fluid-tight seal, adhesive materials may be applied to and between the cover member 12, the tissue regions 422 surrounding the main opening 416, or both of these components. Many different adhesive compounds may be used for this purpose, with the invention not being restricted to any particular compositions or adhesives. For example, commercially-available, epoxy resins, autologous fibrin glue as described in U.S. Pat. No. 4,874,368 to Miller et al. which is incorporated herein by reference, or other conventional medical grade adhesives may be employed. Likewise, the cover member 12 can be sutured in position if needed as determined by clinic diagnosis and review.

Once the cover member 12 is in position as illustrated in FIG. 9, the primary section 36 of the fluid delivery conduit 16 (e.g. the first end 20) and the primary section 70 of the fluid extraction conduit 50 (e.g. the first end 52) are located in the round window niche 410 so that they are directly ahead of and adjacent to the round window membrane 406. This orientation is achieved by proper manipulation of the apparatus 10 within the patient being treated and is likewise accomplished in accordance with the size parameters associated with the apparatus 10 as listed above. As a result of this orientation, fluid materials can be delivered to and from the round window niche 410/round window membrane 406. Regarding the remaining portions of the apparatus 10, the secondary section 40 of the fluid delivery conduit 16 is positioned at least partially within (1) the middle ear 402; and (2) the external auditory canal designated at reference number 424 (FIG. 9). Likewise, the secondary section 72 of the fluid extraction conduit 50 is also located at least partially within the middle ear 402 and external auditory canal 424. This orientation may be accomplished in many ways. For example, as shown in FIG. 9, both the fluid delivery conduit 16 and the fluid extraction conduit 50 pass through the tympanic membrane 426 which preferably has an incision 428 therein that allows the movement of these components (and the other components of the apparatus 10) therethrough. Alternatively, the conduits 16, 50 may pass beneath a tympanomeatal flap (not shown) depending on the techniques chosen by the surgeon. It should likewise be noted that proper orientation of the apparatus 10 within a patient may be accomplished through the use of a conventional operating microscope or otologic endoscope apparatus of the type disclosed in U.S. Pat. No. 5,419,312 to Arenberg et al. which is incorporated herein by reference. In addition, a conventional device known as a "vent tube" may also be optionally used in connection with all of the conduits in each of the embodiments presented herein. Such a device is commercially available from many sources including Micromedix of St. Paul, Minn. (USA)—product no. VT-0301-type 2.

At this point, it is again important to emphasize that the present invention shall not be limited to (A) any methods for placement of the apparatus 10 in position within the ear 400; and (2) any particular orientation in connection with the apparatus 10 provided that the cover member 12 effectively seals the round window niche 410 to create the fluid receiving zone 420 or "inner ear fluid transfer space". Likewise, the apparatus 10 may be maintained in position as previously noted through the use of adhesive materials/sutures which bind the cover member 12 to the tissue regions 422 surrounding the main opening 416 leading into the round window niche 410. If needed and desired as determined by preliminary investigation and clinical review, adhesive materials of the variety listed above may also be applied to any other portions of the apparatus 10 to secure it in position. Packing materials of the type normally used for medical applications can also be employed within the ear 400 to further secure/anchor the apparatus 10 in position if necessary.

To use the apparatus 10 to deliver a selected fluid material (e.g. a therapeutic fluid composition) into the fluid receiving zone 420 within the round window niche 410, a selected fluid delivery device is provided which is schematically illustrated in FIG. 9 at reference number 430. Many different systems can be used in connection with the fluid delivery device 430. For example, the fluid delivery device 430 may involve a standard needle-type syringe apparatus as shown and described in U.S. Pat. No. 5,421,818 or other systems including but not limited to a product which is known as an "osmotic pump." Such a pump is described in Kingma, G. G., et al., "Chronic drug infusion into the scala tympani of the guinea pig cochlea", *Journal of Neuroscience Methods*, 45:127–134 (1992) which is incorporated herein by reference. An exemplary, commercially available osmotic pump may be obtained from the Alza Corp. of Palo Alto Calif. (USA) and is generally described in U.S. Pat. Nos. 4,320, 758 and 4,976,966. However, it should again be noted that the present invention shall not be limited to any particular type of delivery system. In fact, other comparable fluid delivery devices may be used in connection with all embodiments of the invention.

The fluid delivery device 430 (which contains a supply of a selected therapeutic fluid composition 432 therein as defined above) is then activated in order to deliver the therapeutic fluid composition 432 into the second end 22 of the fluid delivery conduit 16. If a syringe is used as the fluid delivery device 430, suitable pressure is exerted on the syringe plunger in order to provide the necessary pressure to transfer the therapeutic fluid composition 432 into the fluid delivery conduit 16. The therapeutic fluid composition 432 then passes through the central passageway 26 of the conduit 16, through the cover member 12 and out of the first end 20 of the conduit 16 into the fluid delivery zone 420. Once the therapeutic fluid composition 432 is within the fluid delivery zone 420, it can subsequently diffuse through the round window membrane 406 and into the inner ear 404 for the treatment of tissues, fluids, fluid compartments, and tissue regions therein. It should again be noted that the claimed invention shall not be restricted to the treatment of any specific inner ear tissues, structures, or compartments. Likewise, passage of the therapeutic fluid composition 432 through the round window membrane 406 takes place in accordance with the unique permeable character of this structure as discussed in detail above and in U.S. Pat. No. 5,421,818.

The fluid extraction conduit 50 may then be used to withdraw any residual fluid materials from the fluid receiving zone 420 if needed and desired in accordance with clinical investigations. The term "residual fluid materials" is defined above and can include a number of different products ranging from excess therapeutic fluid compositions 432 to fluid materials which diffused across the round window membrane 406 from the inner ear 404. This step is accomplished by operative connection of the second end 54 of the fluid transfer conduit 50 to a fluid extracting device 434 which can involve many different systems. For example, the fluid extracting device 434 may consist of a conventional syringe (see U.S. Pat. No. 5,421,818), an osmotic pump system as discussed above, or other known devices suitable for this purpose. To use the fluid extracting device 434, it is initially activated in order to draw the residual fluid materials (designated at reference number 436 in FIG. 9) into the first end 52 of the fluid extraction conduit 50 from the fluid receiving zone 420. If a syringe is used as the fluid extracting device 434, the syringe plunger is drawn outwardly in order to provide the necessary suction force to "pull" the residual fluid materials 436 into the fluid extraction conduit 50. The residual fluid materials 436 then pass into the central passageway 60 of the conduit 50, through the cover member 12, out of the second end 54 of the conduit 50, and into the fluid extracting device 434. In this manner, the residual fluid materials 436 may be completely and effectively removed from the fluid receiving zone 420. It should likewise be noted that the fluid extracting device 434 and fluid delivery device 430 can be operated at any desired intervals including rapid, successive use of these components to achieve a "flushing" of fluid materials into and out of the ear 400. Likewise, the amounts of materials to be delivered and withdrawn from the ear 400 may vary, depending on the clinical diagnosis of the treating physician, with the present invention not being restricted to any particular fluid quantities.

With continued reference to FIG. 9, use of the electrical potential transmission means 74 (which is optional but preferred) will now be discussed. In operation, the proximal end 84 of the elongate conductive member 76/wire 80 (and the attached spherical member 90) are placed adjacent to and in direct physical contact with the round window membrane 406 so that electrical potentials may be received therefrom or transmitted to the membrane 406 as previously noted. Contact between the conductive member 76 and the round window membrane 406 is again accomplished through appropriate physical manipulation of the apparatus 10 and in accordance with the size parameters of the elongate conductive member 76/apparatus 10 described above. Electrical potentials may be generated in the inner ear 404 using externally-generated tone bursts, pips, and the like in accordance with standard ECoG procedures. In a situation where inner ear electrical potentials are to be analyzed, these potentials travel through the inner ear 404 and reach the round window membrane 406 where they are received by the conductive member 76/wire 80. The distal end 86 of the wire 80 is positioned outwardly from the ear 400 as discussed above and is connected to an ECoG monitoring apparatus 94. The monitoring apparatus 94 is used to analyze and quantify electrical potentials (e.g. ECoG potentials) received from the inner ear 404 in response to various stimuli or as an indication of resting potential activity. Further information regarding the monitoring apparatus 94 and its functional capabilities is again provided above (along with an indication that the conductive member 76/wire 80 may also be used in connection with standard iontophoresis procedures.)

At this time, it is important to emphasize that, while the previous discussion involves apparatus 10 with separate fluid delivery and fluid extraction conduits 16, 50, all of the steps, procedures, and methods-of-use associated with the apparatus 10 are equally applicable to apparatus 100 (FIGS. 3–4) which uses a single fluid transfer conduit 102. Thus, the foregoing information regarding use of the apparatus 10 is incorporated by reference in connection with the alternative apparatus 100. The only difference involves operative connection of both the fluid delivery device 430 and fluid extracting device 434 to the second end 106 of the conduit 102, with the supply of therapeutic fluid compositions 432 and the residual fluid materials 436 being transferred into and out of the fluid-receiving zone 420 through the single conduit 102. All of the other techniques and methods associated with apparatus 10 (including placement of the cover member 12 in position) are equally applicable to the apparatus 100. With respect to the alternative apparatus 200 illustrated in FIGS. 5–6, the use of this apparatus will now be discussed.

FIG. 10 again involves a schematic, partial cross-sectional view of the ear 400 of a human subject illustrating the treatment apparatus 200 of FIG. 5 inserted therein. The apparatus 200 is positioned so that the cover member 202 is located entirely within the middle ear, generally designated in FIG. 10 at reference number 402. The inner ear 404 is again denoted in FIG. 9 at reference number 404, with the specific components of the inner ear 404 (including the cochlea, the endolymphatic sac, as well as the endolymphatic duct being omitted for the sake of clarity and described in U.S. Pat. No. 5,421,818). The round window membrane shown at reference number 406 constitutes an interface tissue structure between the middle ear 402 and the inner ear 404. The round window niche is again illustrated at reference number 410 which basically consists of an internal cavity 412, an interior side wall 414, and a main opening 416 leading into the internal cavity 412/round window niche 410.

The initial step in using the apparatus 200 involves placement of the flexible and compressible cover member 202 within the middle ear 402 as illustrated. The cover member 202 is then physically urged into the main opening 416 leading into the round window niche 410 so that the cover member 202 is inserted into the round window niche 410. In accordance with the compressible and resilient nature of the cover member 202, it is readily positioned within the round window niche 410, followed by subsequent expansion of the cover member 202 so that it engages the side wall 414 of the niche 410. As a result, a fluid-tight seal is created which defines the sealed fluid-receiving zone 420 or "inner ear fluid transfer space". The fluid receiving zone 420 is bounded by (1) the cover member 202 which forms an upper boundary; and (2) the round window membrane 406 which forms a lower boundary. The cover member 202 is primarily maintained in position within the round window niche 410 by frictional engagement between the cover member 202 and the side wall 414 of the niche 410. However, in certain cases as determined by routine clinical investigation, adhesive materials may be employed which would be applied to and between the cover member 202, the side wall 414 of the round window niche 410, or both of these components. Many different adhesive compounds may be used for this purpose, with the present invention not being restricted to any particular chemical compositions. For example, commercially-available epoxy resins, autologous fibrin glue as described in U.S. Pat. No. 4,874,368 to Miller et al. which is incorporated herein by reference, or other conventional medical grade adhesives may be employed.

Once the cover member 202 is in position as illustrated in FIG. 10, the primary section 230 of the fluid delivery conduit 210 (e.g. the first end 212) and the primary section 270 of the fluid extraction conduit 250 (e.g. the first end 252) are positioned within the round window niche 410 so that they are directly ahead of and adjacent to the round window membrane 406. This orientation is achieved by proper manipulation of the apparatus 200 in the patient being treated, and is likewise accomplished in accordance with the size parameters associated with the apparatus 200 as listed above. In this manner, fluid materials can be delivered to and withdrawn from the round window niche 410.

With respect to the remaining portions of the apparatus 200, the secondary section 232 of the fluid delivery conduit 210 is at least partially positioned within (1) the middle ear 402; and (2) the external auditory canal 424. Likewise, the secondary section 272 of the fluid extraction conduit 250 is located at least partially within the middle ear 402 and the external auditory canal 424. This orientation may again be accomplished in many ways. For example, as shown in FIG. 10, both the fluid delivery conduit 210 and the fluid extraction conduit 250 (as well as other elements of the apparatus 200) pass through the tympanic membrane 426 which preferably has an incision 428 therein that allows the movement of these components therethrough. Alternatively, the conduits 210, 250 may pass beneath a tympanomeatal flap (not shown) depending on the techniques chosen by the surgeon. It should likewise be noted that proper orientation of the apparatus 200 within a patient may be accomplished through the use of a conventional operating microscope or otologic endoscope apparatus of the type disclosed in U.S. Pat. No. 5,419,312 to Arenberg et al.

At this point, it is again important to emphasize that the present invention shall not be limited to (1) any methods for placement of the apparatus 200 in position within the ear 400; and (2) any particular orientation in connection with the apparatus 200 provided that the cover member 202 effectively seals the round window niche 410 to create the fluid-receiving zone 420 or "inner ear fluid transfer space". The apparatus 200 may again be maintained in position through the use of frictional engagement and/or adhesive materials which bind the cover member 202 to and within the round window niche 410. If needed and desired as determined by preliminary clinical investigations, adhesive compounds of the variety listed above may also be applied to any other portions of the apparatus 200 to secure it in position. Likewise, packing materials of the type normally used for medical applications can be employed within the ear 400 to further secure/anchor the apparatus 200 in its desired location.

To use the apparatus 200 to deliver a selected fluid material (e.g. a therapeutic fluid composition) into the fluid receiving zone 420 within the round window niche 410, a selected fluid delivery device is provided which is again schematically illustrated in FIG. 10 at reference number 430. Many different systems may be used in connection with the fluid delivery device 430 as previously indicated. For example, the fluid delivery device 430 may involve a standard needle-type syringe apparatus (as disclosed in U.S. Pat. No. 5,421,818) or other systems including but not limited to osmotic pumps which are described above.

The fluid delivery device 430 (which contains a supply of a selected therapeutic fluid composition 432 therein) is then activated in order to deliver the therapeutic fluid composition 432 into the second end 214 of the fluid delivery conduit 210. If a syringe is used as the fluid delivery device 430, suitable pressure is exerted on the syringe plunger in order to provide the necessary pressure to deliver the therapeutic fluid composition 432 into the fluid delivery conduit 210. The therapeutic fluid composition 432 then passes through the central passageway 220 of the conduit 210, through the cover member 202, out of the first end 212 of the conduit 210, and into the fluid delivery zone 420. Once the therapeutic fluid composition 432 is within the fluid delivery zone 420, it can then diffuse through the round window membrane 406 and into the inner ear 404 for the treatment of tissues, fluids, fluid compartments, and tissue regions therein. It should again be emphasized that the claimed invention shall not be limited to the treatment of any specific inner ear tissues, structures, or compartments. Likewise, passage of the therapeutic fluid composition 432 through the round window membrane 406 takes place in accordance with the unique permeable character of this structure as discussed in detail above and in U.S. Pat. No. 5,421,818.

The fluid extraction conduit 250 may then be used to withdraw any residual fluid materials from the fluid receiving zone 420 if needed and desired in accordance with clinical investigations. The term "residual fluid materials" is defined above and can include many different products ranging from excess therapeutic fluid compositions to fluid materials which passed across the round window membrane 406 from the inner ear 404. This step is accomplished by operative connection of the second end 254 of the fluid transfer conduit 250 to a fluid extracting device 434 which may again involve a number of different systems. For example, the fluid extracting device 434 can consist of a conventional syringe (as per U.S. Pat. No. 5,421,818), an osmotic pump, or other known devices suitable for this purpose. To use the fluid extracting device 434, it is initially activated in order to draw the residual fluid materials (designated at reference number 436 in FIG. 10) into the first end 252 of the fluid extraction conduit 250 from the fluid-receiving zone 420. If a syringe is used as the fluid extracting device 434, the syringe plunger is drawn outwardly in order to provide the necessary suction force to "pull" the residual fluid materials 436 into the fluid extraction conduit 250. The residual fluid materials 436 then pass into the central passageway 260 of the conduit 250, through the cover member 202, out of the second end 254 of the conduit 250, and into the fluid extracting device 434. In this manner, the residual fluid materials 436 may be effectively removed from the fluid-receiving zone 420. It should likewise be added that the fluid extracting device 434 and fluid delivery device 430 can be operated at any desired intervals including rapid, successive use of these components to achieve a "flushing" of fluid materials into and out of the ear 400. The amounts of materials to be delivered and withdrawn from the ear 400 may vary, depending on the clinical diagnosis of the treating physician, with the present invention not being restricted to any particular fluid quantities.

With continued reference to FIG. 10, use of the electrical potential transmission means 274 (which is optional but preferred) will now be discussed. In operation, the proximal end 284 and attached spherical member 290 of the elongate conductive member 276/wire 280 are placed adjacent to and in direct physical contact with the round window membrane 406 so that electrical potentials may be received therefrom or transmitted to the membrane 406. Contact between the conductive member 276 and the round window membrane 406 is again accomplished through appropriate physical manipulation of the apparatus 200 and in accordance with the size parameters of the conductive member 276/apparatus 200 as previously described. Such potentials may be generated in the inner ear 404 using with externally-generated tone bursts, pips, and the like in accordance with standard ECoG procedures. In a situation where inner ear electrical potentials are to be analyzed, these potentials travel through the inner ear 404 to the round window membrane 406 where they are received by the conductive member 276/wire 280. The distal end 286 of the wire 280 is positioned outwardly from the ear 400 as discussed above and is then connected to the ECoG monitoring apparatus 294. The monitoring apparatus 294 is used to analyze and quantify electrical potentials (e.g., ECoG potentials) received from the inner ear 400 in response to various stimuli or as an indication of resting potential activity. Further information regarding the monitoring apparatus 294 and its functional capabilities is again presented above (along with an indication that the elongate conductive member 276 may also be used in connection with standard iontophoresis procedures.)

While the previous discussion involves apparatus 200 with separate fluid delivery and fluid extraction conduits 210, 250, all of the steps, procedures, and methods-of-use associated with the apparatus 200 are equally applicable to apparatus 300 (FIGS. 7–8) which uses a single fluid transfer conduit 302. Thus, the foregoing information regarding use of the apparatus 200 is incorporated by reference in connection with the alternative apparatus 300. The only difference involves operative connection of both the fluid delivery device 430 and fluid extracting device 434 to the second end 306 of the conduit 302, with the supply of therapeutic fluid compositions 432 and the residual fluid materials 436 being transferred into and out of the fluid-receiving zone 420 through the single conduit 302. All of the other techniques and methods associated with apparatus 200 (including placement of the cover member 202 in position within the round window niche 410) are equally applicable to the apparatus 300.

The present invention involves highly effective methods and devices for delivering fluid materials into and out of the inner ear (as well as conducting diagnostic procedures in connection with inner and middle ear tissue regions). In accordance with the invention, a unique and specially-designed treatment system is provided which is capable of performing a wide variety of basic functions including but not limited to (1) the repeatable and sustained active/passive delivery of therapeutic agents directly into the inner ear through the round window membrane; (2) the simultaneous measurement of inner ear electrical potentials (evoked or otherwise) using ECoG techniques; (3) the controlled withdrawal, exchange, or replacement of inner ear fluid materials via the round window membrane; (4) the delivery of therapeutic fluid compositions to the round window membrane in a manner which is rapid, efficient, controllable, and uses a minimal number of steps and procedures; (5) the transfer of therapeutic fluid compositions to the round window membrane in a highly site-specific manner; (6) the removal of fluid materials from the round window membrane in a localized manner with minimal losses into adjacent tissue regions; (7) the ability to deliver and withdraw/exchange fluid materials from the inner ear at a precisely controlled rate which is readily undertaken using minimally-invasive surgical procedures; and (8) accomplishment of all the above-described goals using a system which is readily applicable to multiple patients having different-sized ear structures. Accordingly, the present invention represents an advance in the art of inner ear treatment, diagnosis, and medicine delivery.

Having herein described preferred embodiments of the invention, it is anticipated that suitable modifications may be made thereto by individuals skilled in the art which nonetheless remain within the scope of the invention. For example, the invention shall not be limited with respect to the construction materials being employed, the size thereof, the fluid materials being delivered/withdrawn, and the physiological environment in which the invention is used. The present invention shall therefore only be construed in accordance with the following claims:

The invention that is claimed is:

1. A method for moving fluid materials through the round window niche and round window membrane of a living subject in order to treat the inner ear thereof, said round window niche comprising an internal cavity therein and a main opening leading into said internal cavity, said method comprising:

providing a medical treatment apparatus comprising:
a cover member sized for placement over said main opening of said round window niche of said subject so that said cover member seals said round window niche in order to form a sealed fluid-receiving zone within said round window niche between said cover member and said round window membrane;
a fluid delivery conduit comprising a first end, a second end, and an internal passageway extending continuously through said fluid delivery conduit from said first end to said second end, said fluid delivery conduit being operatively connected to said cover member so that said fluid delivery conduit can deliver at least one therapeutic fluid composition through said cover member to said fluid-receiving zone during use of said treatment apparatus; and
a fluid extraction conduit comprising a first end, a second end, and an internal passageway extending continuously through said fluid extraction conduit from said first end of said fluid extraction conduit to said second end of said fluid extraction conduit, said fluid extraction conduit being operatively connected to said cover member so that said fluid extraction conduit can remove residual fluid materials from said fluid-receiving zone during use of said treatment apparatus;

inserting said cover member of said treatment apparatus into said middle ear;

positioning said cover member over said main opening of said round window niche in order to seal said main opening so that said sealed fluid-receiving zone is created within said round window niche between said cover member and said round window membrane;

delivering said therapeutic fluid composition into and through said internal passageway of said fluid delivery conduit so that said therapeutic fluid composition passes through said cover member, enters said fluid-receiving zone, and comes in contact with said round window membrane, said therapeutic fluid composition thereafter passing through said round window membrane and into said inner ear for treatment thereof; and withdrawing any of said residual fluid materials which are present within said fluid-receiving zone through said internal passageway of said fluid extraction conduit so that said residual fluid materials can be removed from said subject.

2. The method of claim 1 wherein said withdrawing of said residual fluid materials from said fluid-receiving zone comprises applying suction to said second end of said fluid extraction conduit.

3. The method of claim 1 further comprising:
providing electrical potential transmission means secured to at least one of said fluid delivery conduit and said fluid extraction conduit for transmitting electrical potentials into and out of said inner ear through said round window membrane, said electrical potential transmission means comprising an elongate conductive member affixed to at least one of said fluid delivery conduit and said fluid extraction conduit; and
placing at least a portion of said elongate conductive member in direct contact with said round window membrane.

4. The method of claim 3 further comprising analyzing said electrical potentials received from said inner ear and transmitted through said elongate conductive member.

5. A method for moving fluid materials through the round window niche and round window membrane of a living subject in order to treat the inner ear thereof, said method comprising:

providing a cover member sized to seal said round window niche;

sealing said round window niche with said cover member in order to form a sealed fluid-receiving zone within said round window niche between said cover member and said round window membrane; and delivering a supply of at least one therapeutic fluid composition through said cover member and into said fluid-receiving zone between said cover member and said round window membrane, said therapeutic fluid composition thereafter coming in contact with said round window membrane, passing through said round window membrane, and entering said inner ear for treatment thereof.

6. A method for moving fluid materials through the round window niche and round window membrane of a living subject in order to treat the inner ear thereof, said round window niche comprising an internal cavity therein and a main opening leading into said internal cavity, said method comprising:

providing a medical treatment apparatus comprising:

a cover member sized for placement over said main opening of said round window niche so that said cover member seals said round window niche in order to form a sealed fluid-receiving zone within said round window niche between said cover member and said round window membrane; and a fluid transfer conduit comprising a first end, a second end, and an internal passageway extending continuously through said fluid transfer conduit from said first end to said second end, said fluid transfer conduit being operatively connected to said cover member so that said fluid transfer conduit can deliver at least one therapeutic fluid composition through said cover member to said fluid-receiving zone during use of said apparatus;

inserting said cover member of said treatment apparatus into said middle ear;

positioning said cover member over said main opening of said round window niche in order to seal said main opening so that said fluid-receiving zone is created within said round window niche between said cover member and said round window membrane; and delivering said therapeutic fluid composition into and through said internal passageway of said fluid transfer conduit so that said therapeutic fluid composition passes through said cover member, enters said fluid-receiving zone, and comes in contact with said round window membrane, said therapeutic fluid composition thereafter passing through said round window membrane and into said inner ear for treatment thereof.

7. The method of claim 6 further comprising withdrawing any residual fluid materials which are present within said fluid-receiving zone through said internal passageway of said fluid transfer conduit so that said residual fluid materials can be removed from said subject.

8. The method of claim 6 further comprising:

providing electrical potential transmission means secured to said fluid transfer conduit for transmitting electrical potentials into and out of said inner ear through said round window membrane, said electrical potential transmission means comprising an elongate conductive member affixed to said fluid transfer conduit; and placing at least a portion of said elongate conductive member in direct contact with said round window membrane.

9. A method for moving fluid materials through the round window niche and round window membrane of a living subject in order to treat the inner ear thereof, said round window niche comprising an internal cavity therein and a main opening leading into said internal cavity, said method comprising:

providing a medical treatment apparatus comprising:

a cover member sized for placement over said main opening of said round window niche so that said cover member seals said round window niche in order to form a sealed fluid-receiving zone within said round window niche between said cover member and said round window membrane; and at least one conduit comprising an internal passageway extending continuously through said conduit, said conduit being operatively connected to said cover member; and positioning said cover member of said medical treatment apparatus over said main opening of said round window niche in order to seal said main opening so that said fluid-receiving zone is created within said round window niche between said cover member and said round window membrane.

10. A method for moving fluid materials through the round window niche and round window membrane within the middle ear of a living subject in order to treat the inner ear thereof, said method comprising:

providing a cover member;

inserting said cover member into said middle ear;

positioning said cover member within said middle ear so that said cover member creates a fluid-receiving zone within said round window niche between said cover member and said round window membrane; and delivering a supply of at least one therapeutic fluid composition through said cover member and into said fluid-receiving zone so that said therapeutic fluid composition comes in contact with said round window membrane, passes through said round window membrane, and enters said inner ear for treatment thereof.

* * * * *